US008501885B2

(12) United States Patent
Arriola et al.

(10) Patent No.: US 8,501,885 B2
(45) **Date of Patent: *Aug. 6, 2013**

(54) DUAL- OR MULTI-HEADED CHAIN SHUTTLING AGENTS AND THEIR USE FOR PREPARATION OF BLOCK COPOLYMERS

(75) Inventors: Daniel J. Arriola, Midland, MI (US); Thomas P. Clark, Midland, MI (US); Kevin A. Frazier, Midland, MI (US); Sara B. Klamo, Houston, TX (US); Francis J. Timmers, Midland, MI (US)

(73) Assignee: Dow Global Technologies, LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/377,451

(22) PCT Filed: Jul. 20, 2010

(86) PCT No.: PCT/US2010/042605

§ 371 (c)(1),
(2), (4) Date: Dec. 9, 2011

(87) PCT Pub. No.: WO2011/016991

PCT Pub. Date: Feb. 10, 2011

(65) Prior Publication Data

US 2012/0165486 A1 Jun. 28, 2012

Related U.S. Application Data

(60) Provisional application No. 61/229,610, filed on Jul. 29, 2009.

(30) Foreign Application Priority Data

Jul. 29, 2009 (US) ................................ 61/229,610

(51) Int. Cl.

| | |
|---|---|
| ***C08F 4/44*** | (2006.01) |
| ***C08F 4/52*** | (2006.01) |
| ***B01J 31/00*** | (2006.01) |
| ***C07F 7/08*** | (2006.01) |
| ***C07F 3/00*** | (2006.01) |
| ***C07F 5/06*** | (2006.01) |
| ***C07F 7/02*** | (2006.01) |

(52) U.S. Cl.

USPC ........... 526/183; 526/185; 526/196; 502/152; 502/150; 556/12; 556/129; 556/178; 556/173; 556/128; 556/175

(58) Field of Classification Search

USPC ..... 526/183, 185, 196; 502/152, 150; 556/12, 556/129, 178, 173, 128, 175

See application file for complete search history.

(56) References Cited

U.S. PATENT DOCUMENTS

| | | | |
|---|---|---|---|
| 5,210,338 A | 5/1993 | Samsel | |
| 5,276,220 A | 1/1994 | Samsel et al. | |
| 6,169,151 B1 | 1/2001 | Waymouth et al. | |
| 6,380,341 B1 | 4/2002 | Waymouth et al. | |
| 6,444,867 B1 | 9/2002 | Samsel et al. | |
| 7,355,089 B2 | 4/2008 | Chang et al. | |
| 2006/0199930 A1 | 9/2006 | Li Pi Shan et al. | |
| 2007/0167578 A1 | 7/2007 | Arriola et al. | |
| 2008/0311812 A1 | 12/2008 | Arriola et al. | |
| 2009/0163667 A1 * | 6/2009 | Arriola et al. | 525/240 |

FOREIGN PATENT DOCUMENTS

| | | |
|---|---|---|
| WO | 98/34970 | 8/1998 |
| WO | 2005/090427 A1 | 9/2005 |
| WO | 2007/035485 A1 | 3/2007 |
| WO | 2007/035493 A2 | 3/2007 |
| WO | 2009012215 A1 | 1/2009 |

OTHER PUBLICATIONS

PCT/US2010/042605, International Preliminary Report on Patentability.

PCT/US2010/042605; The International Search Report and; The Writien Opinion of the International; Searching Authority.

Preparation of 1,3-Dizinc Compounds by a Boron-Zinc Exchange. Eick, H.; Knochel, P. Angew. Chern. Int. Ed. Engl. 1996, 35,218-220.

The Direct Formation of Functionalized Alkyl(aryl)zinc Halides by Oxidative Addition of Highly Reactive Zinc with Organic Halides and Their Reactions with Acid Chlorides, a,j}-Unsaturated Ketones, and Allylic, Aryl, and Vinyl Halides. Zhu, L.; Wehmeyer, R. M.; Rieke, R. D. J. Org. Chem. 1991, 56, 1445-1453.

Synthesis of new C2-symmetrical diphosphines using chiral zinc organometallics. Longeau, A.; Durand, S.; Spiegel, A ; Knochel, P. Tetrahedron: Asymmetry 1997, 8, 987-990.

Erdik, Ender et al Erdik, Ender et al: "Reactivities of mixed; organozinc and mixed organocopper reagents, Part 2. Selective n-alkyl; transfer in tri-n-butylphosphine-catalyzed acylation of n-alkylphenylzincs;; an atom economic synthesis of n-alkyl aryl ketones Reactivities of mixed; organozinc and mixed organocopper reagents, Part 2.; Selecti"Tetrahedron Letters, 50(13), 1501-1503 Coden:; Teleay; ISSN: 0040-4039 Tetrahedron Letters, 50(13),; 1501-1503 Coden: Teleay; ISSN: 0040-4039, 2009, XP25937000.

Kim, Young Seok et al Kim, Young Seok et al: "Homogeneous; decomposition mechanisms of diethylzinc by Raman spectroscopy and; quantum chemical calculations Homogeneous decomposition; mechanisms of diethylzinc by Raman spectroscopy and quantum; chemical calculations"Journal of Physical Chemistry A, 112; (18), 4246-4253 Coden: JPCAFH; ISSN: 1089-5639 Journal of; Physical Chemistry A, 112(18), 4246-4253 Coden: JPCAFH;; ISSN: 1089-5639, 2008.

(Continued)

*Primary Examiner* — William Cheung

(57) ABSTRACT

This disclosure relates to olefin polymerization catalysts and compositions, their manufacture, and the production of polyolefins using specific catalyst compositions, including the use of chain shuttling agents in the olefin polymerization process. Specifically, this disclosure provides for dual headed and multi-headed chain shuttling agents (CSAs or MSAs) and for their use in preparing blocky copolymers. By controlling the ratio of dual-headed and multi-headed CSA sites to mono-headed CSA sites, a blocky copolymer can be provided having properties such as a narrow molecular weight distribution and/or improved melt properties.

11 Claims, No Drawings

OTHER PUBLICATIONS

Database CA [Online]; Chemical Abstracts Service, Columbus,; Ohio, US; Fujita, Kenichi et al: "Zinc-containing; dendrimers , their preparation, and their use as Lewis acids", XP002609165, retrieved from STN Database accession No. 2006:886134 abstract.
A Systematic Nomenclature for Cascade Polymers; Newkome, G.R.; Baker, G.R.; Young, J.K.; and Traynham, J.G. Journal of Polymer Science: Part A: Polymer Chemistry, 1993, 31, 641-651.
Lieber and Brintzinger, Macromolecules 2000, 33, 9192-9199.
Liu and Rytter, Macromolecular Rapid Comm. 2001, 22, 952-956.
Bruaseth and Rytter, Macromolecules 2003, 36, 3026-3034.
Rytter, et. al., Polymer 2004, 45, 7853-7861.
Gibson, et al., J. Am. Chem. Soc. 2004, 126, 10701-10712.
Eisch, J. J.; Kotowicz, B. W. Eur. J. Inorg. Chem. 1998, 761-769.
Bhanu Prasad, A. S.; Eick, H.; Knochel, P. J. Organomet. Chem. 1998, 562, 133-139.
J. Organometallic Chem. 1982, 224, 217.

* cited by examiner

DUAL- OR MULTI-HEADED CHAIN SHUTTLING AGENTS AND THEIR USE FOR PREPARATION OF BLOCK COPOLYMERS

This application is the National Stage of International Application No. PCT/US10/42605 filed Jul. 20, 2010, which claims the benefit of U.S. Provisional Application No. 61/229,610 filed Jul. 29, 2009.

FIELD OF THE INVENTION

This disclosure relates to olefin polymerization catalysts and compositions, their manufacture, and the production of polyolefins using specific catalyst compositions, including the use of chain-shuttling agents in the olefin polymerization process.

BACKGROUND OF THE INVENTION

The properties and applications of polyolefins depend to varying degrees upon the specific features of the catalysts used in their preparation. Specific catalyst compositions, activation conditions, steric and electronic features, and the like, all can factor into the characteristics of the resulting polymer product. Indeed, a multitude of polymer features such as co-monomer incorporation, molecular weight, polydispersity, and long-chain branching, and the related physical properties such as density, modulus, melt properties, tensile features, and optical properties, can all be affected by catalyst design.

In recent years, the use of well-defined soluble catalyst precursors generally has allowed enhanced control over polymer properties, including branching architecture, stereochemistry, and block-copolymer construction. This latter aspect of polymer design, in which both "hard" (semicrystalline or high glass transition temperature) blocks and "soft" (amorphous or low glass transition temperature) blocks are assembled in a polymer chain has been especially challenging. Recent advances in block-copolymer formation have been seen with the use of chain-shuttling agents (CSAs) which can exchange a growing polymer chain between different catalytic sites, such that portions of a single polymer molecule are synthesized by at least two different catalysts. In this manner, block copolymers can be prepared from a common monomer environment by using a mixture of catalysts of different selectivities, such as different stereoselectivities or monomer selectivities. Under the right conditions, efficient chain shuttling can produce a multiblock copolymer that features a random distribution of hard and soft blocks of random length.

Generally, the current collection of chain shuttling agents (CSAs) typically contain only a single effective site for chain growth along each polymer chain. Although these CSAs can be considered to contain multiple sites, for example diethyl zinc contains two zinc-ethyl moieties from which a polymer can be attached, chain shuttling between the CSA and catalyst occurs in one direction on each polymer chain. The use of dual-headed CSAs containing an equal number of zinc-alkyl and zinc-alkdiyl groups can potentially lead to reduced homogeneity in the polymer architecture. Such materials can also lead to a broadening of product molecular weight distribution.

Even with the advent of CSA-dual catalyst combinations in block-copolymer preparation, there remain challenges in tailoring the specific copolymer properties that one desires using this approach. Therefore, it is desirable to develop new chain shuttling agents, methods of making the chain shuttling agents, as well as new CSA-catalyst combinations, that can provide new methods to prepare block-copolymers and copolymers with improved properties.

SUMMARY OF THE INVENTION

In some embodiments, the present disclosure provides for a chain shuttling agent having the formula:

$R^1[M^A\text{-}R^2—]_N M^A R^1$, $R^1[M^B R^1—R^2—]_N M^B(R^1)_2$, $M^C[R^2]_2M^C$, or $M^B[R^2]_3M^B$;

or an aggregate thereof, a Lewis base-containing derivative thereof, or any combination thereof; wherein $M^A$ is Zn or Mg;

$M^B$ is B, Al, or Ga;

$M^C$ is Mg;

$R^1$ in each occurrence is independently selected from hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 20 carbon atoms, inclusive;

$R^2$ in each occurrence is independently selected from $(CH_2)_m$, $O[(CH_2)_nCH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]_2$, $(R^B)_3SiOSiR^B[(CH_2)_nCH_2CH_2]_2$, or $[Si(R^B)_2(CH_2)_nCH_2CH_2]_2O$; wherein n in each occurrence is independently an integer from 1 to 20, inclusive; m is an integer from 2 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

In practice, N is the average that describes a sample of molecules and will not necessarily be an integer. For example, N on average can be a number from 5 to 140, from 10 to 125, from 15 to 110, or from 20 to 100, inclusive. The N value of a sample can be determined by NMR spectroscopy or comparable methods.

In these shuttling agent formulas, $R^1$ generally can be selected from any monovalent moiety that does not prevent chain shuttling from occurring. By way of example, $R^1$ is typically selected from a hydrocarbyl such as an alkyl having from 1 to 20 carbon atoms. Also by way of example, $R^2$ can be selected independently from ethandiyl, 1,3-propandiyl, 1,4-butandiyl, 1,5-pentandiyl, 1,6-hexandiyl, 2,5-hexandiyl, 1,7-heptandiyl, 1,8-octandiyl, 1,9-nonandiyl, 1,10-decandiyl, and the like.

In some embodiments, the present disclosure provides for a process for making the chain shuttling agents having the formula $R^1[M^A\text{-}R^2—]_N M^A R^1$, $R^1[M^B R^1—R^2—]_N M^B(R^1)_2$, $M^C[R^2]_2M^C$, or $M^B[R^2]_3M^B$, as described above.

In some embodiments, the present disclosure provides for a catalyst composition comprising the contact product at least one polymerization catalyst precursor, at least one cocatalyst, and at least one shuttling agent as described above. In other embodiments, the present disclosure provides for a process for preparing a catalyst component, the process comprising contacting at least one polymerization catalyst precursor, at least one cocatalyst, and at least one shuttling agent having the formula $R^1[M^A\text{-}R^2—]_N M^A R^1$, $R^1[M^B R^1—R^2—]_N M^B(R^1)_2$, $M^C[R^2]_2 M^C$, or $M^B[R^2]_3 M^B$, as described above.

In some embodiments, the present disclosure provides for a process for the polymerization of at least one addition polymerizable monomer to form a polymer composition, the process comprising:

contacting at least one addition polymerizable monomer with a catalyst composition under polymerization conditions;

the catalyst composition comprising the contact product of at least one polymerization catalyst precursor, at least one cocatalyst, and at least one shuttling agent having the formula $R^1[M^A\text{-}R^2—]_N M^A R^1$, $R^1[M^B R^1—R^2—]_N M^B(R^1)_2$, $M^C[R^2]_2 M^C$, or $M^B[R^2]_3 M^B$, as described above.

In one aspect, this disclosure provides a chain shuttling agent represented by the following Newkome dendrimer nomenclature:

$$[C][(R)\overset{G}{N_b}(Z)]N_c,$$

or an aggregate thereof, a Lewis base-containing derivative thereof, or any combination thereof; wherein:

C is a core selected from a metal, alkdiyl di(metal), alktriyl tri(metal), or alktetrayl tetra(metal), wherein the metal is Zn, Mg, B, Al, or Ga, and any carbon-containing core having from 2 to 50 carbon atoms;

R in each occurrence is a repeat unit selected from an alkdiyl metal, alktriyl di(metal), or alktetrayl tri(metal) having from 2 to 20 carbon atoms and an average branch multiplicity of $N_b$;

G is the generation of the dendrimer cascade;

Z is a terminal monovalent group having up to 20 carbon atoms;

$N_c$ is the branch multiplicity of the core; and the shuttling agent comprises at least one generation of repeat unit R, such that G, on average, is an number from 2 to 150, inclusive.

In practice, G is the average generational description of a sample of molecules and will not necessarily be an integer. The G and N of a sample can be determined by NMR spectroscopy or comparable methods.

This disclosure also provides a process for the polymerization of at least one addition polymerizable monomer to form a polymer composition, the process comprising:

contacting at least one addition polymerizable monomer with a catalyst composition under polymerization conditions;

the catalyst composition comprising the contact product of at least one polymerization catalyst precursor, at least one cocatalyst, and at least one chain shuttling agent as described above.

This disclosure also provides for a catalyst composition comprising the contact product of least one polymerization catalyst precursor, at least one cocatalyst, and at least one shuttling agent represented by the Newkome dendrimer nomenclature above. This disclosure also provides for a process for preparing such a catalyst component, the process comprising contacting at least one polymerization catalyst precursor, at least one cocatalyst, and at least one shuttling agent of this Newkome dendrimer nomenclature.

In some embodiments, the present disclosure provides for a process for making the chain shuttling agents having the formulas $$[C][(R)\overset{G}{N_b}(Z)]N_c,$$

as described above.

While the Newkome nomenclature is not a molecular formula in the traditional sense, it does constitute a shorthand by which one of ordinary skill in the art can understand the traditional molecular formula. According to the Newkome nomenclature parameters, because G is an number from 2 to 150, there is at least one repeat unit in the dendritic chain shuttling agent of this disclosure.

As understood by one of ordinary skill, the branch multiplicity of the core ($N_c$) is two for zinc and for an alkdiyl di(metal), three for an alktriyl tri(metal), and four for an alktetrayl tetra(metal). However, the branch multiplicity $N_b$ of the repeat unit R is one for an alkandiyl metal, two for an alkantriyl di(metal), and three for an alkantetrayl tri(metal).

Another aspect of this disclosure is that the chain shuttling agents such as $R^1[M^A\text{-}R^2—]_N\text{-}M^A R^1$ and $R^1[M^B R^1—R^2—]_N M^B(R^1)_2$ disclosed herein constitute CSAs that typically can be described by the Newkome dendrimer nomenclature $$[C][(R)\overset{G}{N_b}(Z)]N_c.$$

A further aspect of this disclosure relates to the preparation and utility of catalyst compositions having new structural entities containing repeating units of main group metals and alkandiyl groups, such as -alkandiyl-zinc-alkandiyl-zinc-alkandiyl-, and so forth. Such structures can function as dual headed CSAs and can be used in block-type polymerization reactions. For example, when the monomer feed or concentration is altered during a copolymerization process, symmetric gradient triblock copolymers can be formed. The process can be extended to form a symmetric multiblock copolymer with an odd number of blocks, with those blocks having either a gradual or a sharp gradient in composition or crystallinity. In a further aspect, this disclosure provides for compositions comprising or selected from the polymeric and heteroatom substituted CSAs disclosed herein, and processes for making and using them, and compositions of the product polymers.

Accordingly, one aspect of the present disclosure provides an olefin polymer composition characterized by a narrow molecular weight distribution and a process for preparing the olefin polymer composition. The polymer composition is prepared in situ by the polymerization of one or more addition polymerizable monomers, generally of two or more addition polymerizable monomers, particularly ethylene and at least one copolymerizable comonomer, propylene and at least one copolymerizable comonomer having 4 or more carbons, or 4-methyl-1-pentene and at least one different copolymerizable comonomer having 4 or more carbons, optionally comprising multiple blocks or segments of differentiated polymer composition or properties, especially blocks or segments comprising differing comonomer incorporation levels. In this aspect, the present process includes contacting an addition polymerizable monomer or mixture of monomers under addition polymerization conditions with a composition comprising at least one addition polymerization catalyst, a cocatalyst and a dual-headed or multi-headed chain shuttling agent as provided herein.

Further, this disclosure provides a process for forming an n-block copolymer where n is an odd number greater than or equal to 3, the process comprising contacting at least one addition polymerizable monomer with a catalyst composition under polymerization conditions; the catalyst composition comprising at least one polymerization catalyst precursor, at least one cocatalyst, and at least one shuttling agent as disclosed herein; wherein the process comprises (n+1)/2 combination chain transfer and growth steps.

DETAILED DESCRIPTION OF THE INVENTION

The term "shuttling agent" or "chain shuttling agent" refers to a compound or mixture of compounds that is capable of causing polymeryl transfer between various active catalyst sites under conditions of polymerization. That is, transfer of a polymer fragment occurs both to and from an active catalyst site in a facile and reversible manner. In contrast to a shuttling agent, an agent that acts merely as a chain transfer agent such as some main-group alkyl compounds, may exchange, for example, an alkyl group on the chain transfer agent with the growing polymer chain on the catalyst, which generally results in termination of the polymer chain growth. In this event, the main-group center may act as a repository for a dead polymer chain, rather than engaging in reversible transfer with a catalyst site in the manner in which the chain shuttling agent does. Desirably, the intermediate formed between the chain shuttling agent and the polymeryl chain is not sufficiently stable relative to exchange between this intermediate and any other growing polymeryl chain, such that chain termination is relatively rare.

The multi- or dual-headed shuttling agents include species with metal-alkyl bonds that engage in chain transfer during a transition-metal catalyzed polymerization. Because these chain shuttling agents can be oligomeric, can consist of blends of species, or both, it is difficult to precisely describe these agents because as they are used in solution, the CSA solution typically comprises a complex mixture of different species. Therefore the useful CSAs disclosed here are typically described using average compositions, average numbers of multi-headed site valencies, average numbers of single-headed site valencies, and ratios of these numbers. For example, in CSAs having the empirical formulas $M^B[R^2]_3M^B$ or $M^C[R^2]_2M^C$ as disclosed here ($M^B$ is B, Al, or Ga and $M^C$ is Mg), these products are typically not discrete dimeric structures suggested by their empirical formulas, but rather these formulas or descriptions are representative of the empirical formulas of the polymeric CSA structures.

The term, "dual-headed" or "multi-headed" shuttling agent (or chain shuttling agent) refers to a compound or molecule containing more than one chain shuttling moiety joined by a polyvalent linking group. By way of illustration, one example of a dual-headed CSA is provided in the compounds of the general formulas $R^1—[Zn—R^2—]_NZn—R^1$ or $R^1$-$[AlR^1—R^2—]_NAlR^1{}_2$, in which $R^1$ is a monovalent hydrocarbyl group and $R^2$ is a divalent hydrocarbadiyl group. Further by way of illustration, one example of a tri-headed CSA is provided in the compounds of the general chemical formulas $(R^3Zn_3)[(R^3(ZnR^1)_2]_3$, in which $R^1$ is a monovalent hydrocarbyl group such as ethyl, and $R^3$ is a trivalent hydrocarbatriyl group. For a trivalent hydrocarbatriyl chain shuttling agent, up to three polymer growth residues are possible, each connected to the trivalent residue. A single polymer growth residue can be comprised of concantated segments from multiple catalysts. It is desirable to have all valencies of the $R^3$ moiety participate in this chain growth activity which will lead to the highest molecular weight polymer. In practice, suitable chain shuttling moieties typically include metal centers derived from a metal selected from Groups 2-14 of the Periodic Table of the Elements and having one or more available valencies capable of reversibly binding a growing polymer chain prepared by a coordination polymerization catalyst. At the same time that the chain shuttling moiety binds to the growing polymer chain, the remnant of the polyvalent linking group remaining after loss of the chain shuttling moiety or moieties incorporates or otherwise bonds to one or more active catalyst sites, thereby forming a catalyst composition containing an active coordination polymerization site capable of polymer insertion at least one terminus of what was originally the polyvalent linking group Many chain shuttling agents of this disclosure can be considered "dendritic", with the dual-headed CSAs constituting one type of dendritic CSA. One convenient and systematic nomenclature to describe dendrimers or "cascade" polymers or oligomers is reported in "A Systematic Nomenclature for Cascade Polymers;" Newkome, G. R.; Baker, G. R.; Young, J. K.; and Traynham, J. G. *Journal of Polymer Science: Part A: Polymer Chemistry,* 1993, 312, 641-651, which is incorporated by reference herein in its entirety. The Newkome nomenclature can be adapted to describe a wide range of dual- and multi-headed CSAs having combinations of different multi-, dual-, and mono-headed sites.

In some embodiments, the present disclosure provides for a series of dual-headed and multi-headed chain transfer agents that limit, reduce, or minimize the number of zinc-alkyl end groups or mono-headed CSA sites $R^1$, in comparison with the dual-headed $R^2$ or multi-headed $R^3$ or $R^4$ CSA sites, a feature which has been discovered to lead to a more homogeneous polymer. This aspect, in turn, may be reflected in more desirable polymer properties, such as a more narrow molecular weight distribution as compared to polymers resulting from chain transfer agents without such limits. In one aspect, the chain shuttling agent can be a dual-headed CSA with the ratio of $R^2$ sites to $R^1$ sites being greater than 1. Thus, by controlling the ratio of multi-headed to mono-headed site valencies, Q, to values greater than one (Q>1), this disclosure leads to block polymeric materials with narrower molecular weight distributions than those obtained from diethylzinc or from dual-headed CSAs having the ratio Q=1.

The parameter Q, is defined as the ratio of the number of multi-headed site valencies to the number of single site valencies in an empirical formula in the chain shuttling agent or agents. Thus, each $R^1$ group is considered as having one single site valency, each $R^2$ group is considered as having two dual-headed site valencies, that is, valencies of the twofold type, each $R^3$ is considered as possessing three three-headed or threefold type site valencies, and each $R^4$ is considered as four valencies of the fourfold type, and so forth. Therefore, if R1, R2, R3, R4, and so forth up to Rn, represent the number of $R^1$, $R^2$, $R^3$, $R^4$ and Rn moieties or groups, respectively, in the empirical formula of a chain shuttling agent, then Q can be defined by the following formula:

$$Q=(2\cdot R2+3\cdot R3+4\cdot R4+\ldots n\cdot Rn)/R1.$$

A similar series of aluminum chain shuttling agents is also encompassed by this disclosure, with corresponding features that limit the ratio of $R^2$ sites to $R^1$ sites. Moreover, in another aspect, appropriate use of anionic heteroatom substitution, such as halide or alkoxide, on M can be used to decrease the value of R1 and therefore increase Q to higher values approaching infinity.

A further aspect of this disclosure is the use of dual headed CSAs as disclosed herein for the preparation of symmetric multiblock copolymers with an odd number of blocks (n=3, 5, 7, and so forth), and a monomer gradient separating the blocks.

In one aspect, the present disclosure provides for dual-headed and multi-headed chain shuttling agents (CSAs) and for their use in preparing block copolymers having desired properties. Among other things, the present disclosure provides for the design and utility of CSAs in an olefin polymerization process, in which the ratio (Q) of dual-headed CSA site valencies (for example, alkdiyl or $R^2$) or multi-headed CSA site valencies (for example, alktriyl ($R^3$) or alktetrayl ($R^4$)) to mono-headed CSA site valencies (for example, alkyl or any monovalent $R^1$) are regulated. By controlling the ratio of $R^2$, $R^3$ or $R^4$ dual- or multi-headed CSA site valencies to $R^1$ (monovalent) mono-headed or "terminal" CSA site valencies, typically to values greater than 1, multi-block copolymers having tailored properties such as narrow molecular weight distributions or improved melt properties are provided. For example, by controlling the ratio of dual-headed and multi-headed CSA sites to mono-headed CSA sites (for example, $R^1$ such as alkyl) to values greater than 1, a more homogeneous CSA may be obtained resulting in more homogeneous polymers with improved properties such as narrowing of the molecular weight distribution or improved melt properties. This class of reagents provides a chemical alternative to process condition control of polymer homogeneity.

In various aspects, the following references are related generally to zinc and aluminum compounds, each of which is hereby incorporated by reference in its entirety.

Preparation of 1,3-Dizinc Compounds by a Boron-Zinc Exchange. Eick, H.; Knochel, P. *Angew. Chem. Int. Ed. Engl.* 1996, 35, 218-220; The Direct Formation of Functionalized Alkyl(aryl)zinc Halides by Oxidative Addition of Highly Reactive Zinc with Organic Halides and Their Reactions with Acid Chlorides, α,β-Unsaturated Ketones, and Allylic, Aryl, and Vinyl Halides. Zhu, L.; Wehmeyer, R. M.; Rieke, R. D. *J. Org. Chem.* 1991, 56, 1445-1453; Synthesis of New $C_2$-Symmetrical Diphosphines using Chiral Zinc Organometallics. Longeau, A.; Durand, S.; Spiegel, A.; Knochel, P. *Tetrahedron: Asymmetry* 1997, 8, 987-990; Control of Polymer Architecture and Molecular Weight Distribution via Multi-Centered Shuttling Agent. Carnahan, E.; Hustad, P.; Jazdzewski, B. A.; Kuhlman, R. L.; Wenzel, T.; WO 2007/035493 A2; and Catalytic Olefin Block Copolymers with Controlled Block Sequence Distribution. Wenzel, T.; Carnahan, E.; Kuhlman, R. L.; Hustad, P. D.; WO 2007/035485 A1.

The following references also are related generally to various aspects of this disclosure, for example, chain transfer agents, each of which is hereby incorporated by reference in its entirety: Lieber and Brintzinger, *Macromolecules* 2000, 33, 9192-9199; Liu and Rytter, *Macromolecular Rapid Comm.* 2001, 22, 952-956; and Bruaseth and Rytter, *Macromolecules* 2003, 36, 3026-3034; Rytter, et. al., *Polymer* 2004, 45, 7853-7861; WO 07/35493; WO 98/34970; Gibson, et al., *J. Am. Chem. Soc.* 2004, 126, 10701-10712; and U.S. Pat. Nos. 6,380,341; 6,169,151; 5,210,338; 5,276,220; and 6,444,867.

Another aspect of the present disclosure provides for the preparation of new structural entities containing repeating units of main group metals such as zinc, aluminum, magnesium, boron, or gallium, and alkandiyl groups (for example, containing repeating moieties such as -alkadiyl-zinc-alkadiyl-zinc). In this disclosure, the terms alkandiyl, alkadiyl, and alkdiyl are used interchangeably. These structures are considered dual headed CSAs and can be used in block-type polymerization reactions. For example, when the monomer feed or concentration is changed during a copolymerization, symmetric gradient triblock copolymers can be formed. The process can be extended to form a symmetric multiblock copolymer with an odd number of blocks with those blocks having either gradual or sharp gradient in composition or crystallinity As disclosed here, one aspect provides for a batch reaction with ethylene and propylene and an activated catalyst using the dual-headed CSAs as disclosed herein. Because ethylene generally has a substantially higher reactivity than propylene, the propylene is added to excess as the reaction is run beyond full consumption of the limiting ethylene reagent. The final polymer morphology can include an ethylene/propylene rubber segment with isotactic propylene on each end.

Yet a further aspect of this disclosure provides for the use of dual-headed CSAs as described here, along with the addition of diethyl zinc or other single site CSA moieties which can create inhomogeneity. The relative amount of the inhomogeneity can be controlled by adding either more or less diethyl zinc to the reactor. Moreover, additional blocks can be added to the end of the polymer by, for example, the addition of another monomer or by transferring the reaction mixture to another reactor.

In one aspect, the present disclosure provides for inventive polymer products that include combinations of two or more polymers comprising regions or segments (blocks) of differing chemical composition or physical properties. Because the polymer composition can contain a linking group which is the remnant of a multi-centered shuttling agent, the resulting polymeric composition may possess unique physical and chemical properties compared to random mixtures of polymers of the same gross chemical composition and compared to block copolymers prepared with a chain shuttling agent lacking the dual-headed or multi-headed chain shuttling centers. Depending on the number of active centers in the dual- or multi-headed chain shuttling agent, that is, whether each shuttling agent molecule has two, three, or more active shutting sites, and the number of separate additions of such agent, the resulting polymer may be relatively monodisperse, form a controllable distribution of molecular weight polymers and/or branched or multiply branched polymers. In general, the resulting polymers contain reduced incidence of crosslinked polymer formation evidenced by reduced gel fraction. For example, typically the polymers produced according to this disclosure comprise less than 2 percent of a crosslinked gel fraction, more preferably less than 1 percent crosslinked gel fraction, and most preferably less than 0.5 percent of crosslinked gel fraction.

Thus, in one aspect, disclosed herein is a process for the polymerization of at least one addition polymerizable monomer to form a polymer composition, the process comprising:

contacting at least one addition polymerizable monomer with a catalyst composition under polymerization conditions;

the catalyst composition comprising the contact product of at least one polymerization catalyst precursor, at least one cocatalyst, and at least one shuttling agent represented by the following Newkome dendrimer nomenclature:

$$[C][(R)\overset{G}{N_b}(Z)]N_c,$$

or an aggregate thereof, a Lewis base-containing derivative thereof, or any combination thereof; wherein:

C is a core selected from a metal, alkandiyl di(metal), alkantriyl tri(metal), or alkantetrayl tetra(metal), wherein the metal is Zn, Mg, B, Al, or Ga, and any carbon-containing core has from 2 to 50 carbon atoms;

R in each occurrence is a repeat unit selected from an alkandiyl metal, alkantriyl di(metal), or alkantetrayl tri (metal) having from 2 to 20 carbon atoms and an average branch multiplicity of $N_b$;

G is the generation of the dendrimer cascade;

Z is a terminal monovalent group having up to 20 carbon atoms;

$N_c$ is the branch multiplicity of the core; and the shuttling agent comprises at least one generation of repeat unit R, such that G, on average, is an number from 2 to 150, inclusive.

In practice, G is the average generational description of a sample of molecules and will not necessarily be an integer. The G and N of a sample can be determined by NMR spectroscopy or comparable methods.

Also provided is a catalyst composition comprising the contact product of at least one polymerization catalyst precursor, at least one cocatalyst, and at least one shuttling agent represented by the Newkome dendrimer nomenclature immediately above.

While the Newkome nomenclature is not a molecular formula in the traditional sense, it does constitute a shorthand by which one of ordinary skill can understand the traditional molecular formula. According to the Newkome nomenclature parameters, because G is an integer from 2 to 150, there is at least one repeated unit in the dendritic chain shuttling agent of this disclosure. In a further aspect, G can be from 2 to 100, from 2 to 50, or from 2 to 25, as well as ranges and sub-ranges between.

The present disclosure also provides a process for the polymerization of at least one addition polymerizable monomer to form a polymer composition, the process comprising:

contacting at least one addition polymerizable monomer with a catalyst composition under polymerization conditions;

the catalyst composition comprising the contact product of at least one polymerization catalyst precursor, at least one cocatalyst, and at least one shuttling agent having the formula:

$R^1[M^A\text{-}R^2—]_N M^A R^1$, wherein $M^A$ is Zn or Mg, $R^1[M^B R^1—R^2—]_N M^B(R^1)_2$, wherein $M^B$ is B, Al, or Ga, or $M^C[R^2]_2M^C$, wherein $M^C$ is Mg, $M^B[R^2]_3M^B$, wherein $M^B$ is B, Al, or Ga, as provided above;

or an aggregate thereof, a Lewis base-containing derivative thereof, or any combination thereof; wherein $R^1$ in each occurrence is independently a monovalent group such as hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 30 carbon atoms;

$R^2$ in each occurrence is independently selected from $(CH_2)_m$, $O[(CH_2)_nCH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]_2$, $(R^B)_3SiOSiR^B[(CH_2)_nCH_2CH_2]_2$, or $[Si(R^B)_2(CH_2)_nCH_2CH_2]_2O$; wherein n in each occurrence is independently an integer from 1 to 20, inclusive; m is an integer from 2 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

In these shuttling agent formulas, $R^1$ can be selected from any monovalent moiety that does not prevent chain shuttling from occurring. Specific examples of $R^1$ include, but are not limited to, $CH_3$, $CH_2CH_2$, $CH_2CH_2CH_3$, $CH_2CH_2CH_2CH_3$, $CH(CH_3)_2$, $CH_2CH(CH_3)_2$, $CF_3$, $C_6H_5$, $C_6H_4CH_3$, Cl, Br, I, $OCH_3$, $OCH_2CH_2$, $OCF_3$, $OC_6H_5$, $OCH_2CH_2CH_3$, $OCH(CH_3)_2$, $OC_6H_5$, $OC_6H_4CH_3$, $OC_6H_3(CH_3)_2$, $OC_6H_2(CH_3)_3$, $SCH_3$, $SCH_2CH_2$, $SC_6H_5$, $NH_2$, $NHCH_3$, $NHCH_2CH_2$, $NHCH_2CH_2CH_3$, $NHCH(CH_3)_2$, $NHC_6H_5$, $NHC_6H_4CH_3$, $N(CH_3)_2$, $N(CH_2CH_2)_2$, $Si(CH_3)_3$, $Si(CH_2CH_3)_3$, and the like, although typically $R^1$ can be selected from a hydrocarbyl such as those specific moieties exemplified here.

This disclosure also provides for a catalyst composition comprising the contact product of least one polymerization catalyst precursor, at least one cocatalyst, and at least one shuttling agent having the formulas presented immediately above. A number of dual-headed and multi-centered chain shuttling agents have been described herein that can be generally characterized by either the Newkome dendrimer nomenclature $$[C][(R)\overset{G}{N}_b(Z)]N_c,$$

or by the general formulas $R^1[M^A\text{-}R^2—]_N M^A R^1$, $R^1[M^B R^1—R^2—]_N M^B(R^1)_2$, $M^C[R^2]_2M^C$, or $M^B[R^2]_3M^B$. When the CSAs can be described using the Newkome dendrimer nomenclature $$[C][(R)\overset{G}{N}_b(Z)]N_c,$$

such species are characterized by having a generation of the dendrimer cascade G>1. When the CSAs can be described using the linear CSA formulas $R^1[M^A\text{-}R^2—]_N M^A R^1$ and $R^1[M^B R^1—R^2—]_N M^B(R^1)_2$, such species are characterized by having N>1.

The CSAs of this disclosure have a generation of the dendrimer cascade G greater than 1, or have an N in the formulas $R^1[M^A\text{-}R^2—]_N M^A R^1$ and $R^1[M^B R^1—R^2—]_N M^B(R^1)_2$ greater than 1. Specific examples include compounds of the formulas $Et[Zn(CH_2)_n]_xZnEt$, in which n can be 2, 3, 4, 5, 6, 7, 8, 9, 10, 12, 15, 20, and the like, and x can be 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or greater, or $Et[AlEt(CH_2)_m]_yAlEt_2$, in which m can be 2, 3, 4, 5, 6, 7, 8, 9, 10, 12, 15, 20, and the like, and y can be 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or greater. Any particular sample of $R^1[M^A\text{-}R^2—]_N M^A R^1$ and $R^1[M^B R^1—R^2—]_N M^B(R^1)_2$ is expected to contain blends or mixtures of different species, having a range of values of N. Formulas such as $R^1[M^A\text{-}R^2—]_N M^A R^1$ and $R^1[M^B R^1—R^2—]_N\text{-}M^B(R^1)_2$ as used this disclosure are intended to reflect a population of molecules, characterized by a range or distribution of N values. Therefore, unless provided otherwise, values of N are stated as average values for the mixture of species in a particular sample, as evidenced by the ratio of $R^2$ to $R^1$ moieties which can be determined by, for example, $^1H$ NMR.

Further examples of the chain shuttling agents of this disclosure include compounds of the formulas $X[ZnR^2]_xZnX$ or $X[AlX(R^2)]_yAlX_2$, where $R^2$ is an alkdiyl moiety such as $CH_2CH_2$, and where x and y are integers greater than 1 and where X is selected independently from $CH_3$, $CH_2CH_2$, $CH_2CH_2CH_3$, $CH_2CH_2CH_2CH_3$, $CH(CH_3)_2$, $CH_2CH(CH_3)_2$, $C_6H_5$, $C_6H_4CH_3$, Cl, Br, I, $OCH_3$, $OCH_2CH_2$, $OC_6H_5$, $OCH_2CH_2CH_3$, $OCH(CH_3)_2$, $OC_6H_5$, $OC_6H_4CH_3$, $OC_6H_3(CH_3)_2$, $OC_6H_2(CH_3)_3$, $SCH_3$, $SCH_2CH_2$, $SC_6H1_5$, $NH_2$, $NHCH_3$, $NHCH_2CH_2$, $NHCH_2CH_2CH_3$, $NHCH(CH_3)_2$, $NHC_6H_5$, $NHC_6H_4CH_3$, $N(CH_3)_2$, $N(CH_2CH_2)_2$, $Si(CH_3)_3$, $Si(CH_2CH_3)_3$, and the like.

Monomers

Suitable monomers for use in preparing the copolymers of the present disclosure include any addition polymerizable monomer, generally any olefin or diolefin monomer. Suitable monomers can be linear, branched, acyclic, cyclic, substituted, or unsubstituted. In one aspect, the olefin can be any α-olefin, including, for example, ethylene and at least one different copolymerizable comonomer, propylene and at least one different copolymerizable comonomer having from 4 to 20 carbons, or 4-methyl-1-pentene and at least one different copolymerizable comonomer having from 4 to 20 carbons. Examples of suitable monomers include, but are not limited to, straight-chain or branched α-olefins having from 2 to 30 carbon atoms, from 2 to 20 carbon atoms, or from 2 to 12 carbon atoms. Specific examples of suitable monomers include, but are not limited to, ethylene, propylene, 1-butene, 1-pentene, 3-methyl-1-butene, 1-hexane, 4-methyl-1-pentene, 3-methyl-1-pentene, 1-octene, 1-decene, 1-dodecene, 1-tetradecene, 1-hexadecene, 1-octadecene, and 1-eicosene. Suitable monomers for use in preparing the copolymers disclosed herein also include cycloolefins having from 3 to 30, from 3 to 20 carbon atoms, or from 3 to 12 carbon atoms. Examples of cycloolefins that can be used include, but are not limited to, cyclopentene, cycloheptene, norbornene, 5-methyl-2-norbornene, tetracyclododecene, and 2-methyl-1,4,5,8-dimethano-1,2,3,4,4a,5,8,8a-octahydronaphthalene. Suitable monomers for preparing the copolymers disclosed herein also include di- and poly-olefins having from 3 to 30, from 3 to 20 carbon atoms, or from 3 to 12 carbon atoms. Examples of di- and poly-olefins that can be used include, but are not limited to, butadiene, isoprene, 4-methyl-1,3-pentadiene, 1,3-pentadiene, 1,4-pentadiene, 1,5-hexadiene, 1,4-hexadiene, 1,3-hexadiene, 1,3-octadiene, 1,4-octadiene, 1,5-octadiene, 1,6-octadiene, 1,7-octadiene, ethylidene norbornene, vinyl norbornene, dicyclopentadiene, 7-methyl-1,6-octadiene, 4-ethylidene-8-methyl-1,7-nonadiene, and 5,9-dimethyl-1,4,8-decatriene. In a further aspect, aromatic vinyl compounds also constitute suitable monomers for preparing the copolymers disclosed here, examples of which include, but are not limited to, mono- or poly-alkylstyrenes (including styrene, o-methylstyrene, m-methylstyrene, p-methylstyrene, o,p-dimethylstyrene, o-ethylstyrene, m-ethylstyrene and p-ethylstyrene), and functional group-containing derivatives, such as methoxystyrene, ethoxystyrene, vinylbenzoic acid, methyl vinylbenzoate, vinylbenzyl acetate, hydroxystyrene, o-chlorostyrene, p-chlorostyrene, divinylbenzene, 3-phenylpropene, 4-phenylpropene and α-methylstyrene, vinylchloride, 1,2-difluoroethylene, 1,2-dichloroethylene, tetrafluoroethylene, and 3,3,3-trifluoro-1-propene, provided the monomer is polymerizable under the conditions employed.

Further, in one aspect, suitable monomers or mixtures of monomers for use in combination with at least one dual and multi-headed chain shuttling agent disclosed here include ethylene; propylene; mixtures of ethylene with one or more monomers selected from propylene, 1-butene, 1-hexene, 4-methyl-1-pentene, 1-octene, and styrene; and mixtures of ethylene, propylene and a conjugated or non-conjugated diene. In this aspect, the copolymer or interpolymer can contain two or more intramolecular regions comprising differing chemical or physical properties, especially regions of differentiated comonomer incorporation, joined in a dimeric, linear, branched or polybranched polymer structure. Such polymers may be prepared by altering the polymerization conditions during a polymerization that includes a dual-headed or multi-headed chain shuttling agent, for example by using two reactors with differing comonomer ratios, multiple catalysts with differing comonomer incorporation abilities, or a combination of such process conditions, and optionally a polyfunctional coupling agent.

In one aspect of this polymerization system, while attached to the growing polymer chain, the shuttling agent desirably does not alter the polymer structure or incorporate additional monomer. That is, the shuttling agent typically does not also possess significant catalytic properties for polymerization. Rather, the shuttling agent can form a metal-alkyl or other type of interaction with the polymer moiety until transfer of the polymer moiety to an active polymerization catalyst site again occurs. Transfer of the same shuttling agent site back to the original catalyst merely results in an increase in polymer molecular weight. In contrast, transfer to a different catalyst, if more than one catalyst type is employed, results in the formation of a distinguishable polymer type, due for example, to a difference in monomer incorporation properties, tacticity, or other property of the subsequent catalyst. Transfer by means of one of the remaining shuttling sites results in growth from a different point in the polymer molecule. With a two-headed or -centered shuttling agent, at least some of the resulting polymer is approximately double the molecular weight of remaining polymer segments. Under certain circumstances, the subsequently formed polymer region also possesses a distinguishable physical or chemical property, such as a different monomer or comonomer identity, a difference in comonomer composition distribution, crystallinity, density, tacticity, regio-error, or other property, compared to the polymer formed at other times during the polymerization. Subsequent repetitions of the foregoing process can result in formation of segments or blocks having a multiplicity of differing properties, or a repetition of a previously formed polymer composition, depending on the rates of polymeryl exchange, the number of reactors or zones within a reactor, the transport features between the reactors or zones, the number of different catalysts, the monomer gradient in the reactor(s), and so forth.

Transfer of the growing polymer can occur multiple times with continued growth of a polymer segment each time it is attached to an active catalyst. Under uniform polymerization conditions, the growing polymer blocks can be substantially homogeneous, though their size conforms to a distribution of sizes, for example, a most probable distribution of sizes. Under differing polymerization conditions such as the presence of different monomers or monomer gradients in a reactor, multiple reactors operating under differing process conditions, and so forth, the respective polymer segments also may be distinguished based on differences in chemical or physical properties. Chain shuttling and further growth may continue in this described manner for any number of cycles.

CSAs and Their Preparation

Examples of some chain shuttling agents and their Newkome nomenclature are provided in the following Table 1. These examples include general linker and core groups of the general type $R^n$, where n is the valence of the particular group, examples of which include alkyl ($R^1$), alkdiyl ($R^2$), alktriyl ($R^3$), and alktetrayl ($R^4$), although $R^1$ through $R^4$ are not limited strictly to hydrocarbyl-type moieties, for example, alkyl, halide, and alkoxy all constitute $R^1$ moieties. As used throughout, the terms alkadiyl or alkandiyl also may be used to refer to a divalent alkdiyl ($R^2$) moiety, just as alkatriyl or alkantriyl may be used to refer to the trivalent alktriyl ($R^3$) moiety, and alkatetrayl or alkantetrayl may be used to refer to the tetravalent alktetrayl ($R^4$) moieties, respectively. The CSA structures in Table 1 are not intended to be limiting but are illustrations of average stoichiometries or empirical formulas, as provided herein.

TABLE 1

Examples of Inventive Chain Shuttling Agents and Their Newkome Nomenclature, $[C][(R)\overset{G}{N}_b(Z)]N_c$.

| Chain Shuttling Agent | $[C][(R)\overset{G}{N}_b(Z)]N_c$ |
|---|---|
| 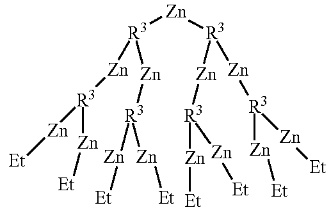 | $[Zn][(R^3Zn_2)_2{}^2(Et)]_2$ |
| 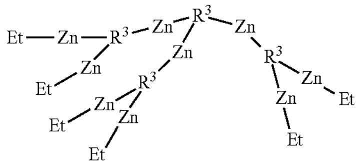 | $[R^3Zn_3][(R^3Zn_2)_2{}^1(Et)]_3$ |
| 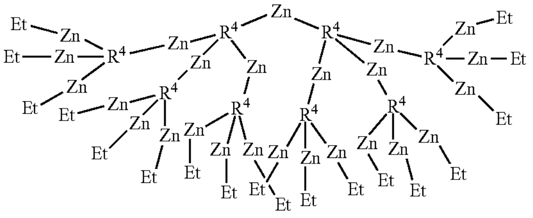 | $[Zn][(R^4Zn_3)_3{}^2(Et)]_2$ |
| 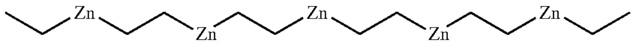 | $[Zn][(CH_2CH_2Zn)_1{}^2(Et)]_2$ |
| 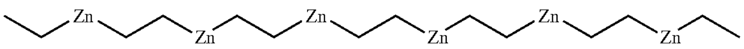 | $[Zn(CH_2)_2Zn][(CH_2CH_2Zn)_1{}^2(Et)]_2$ |
| 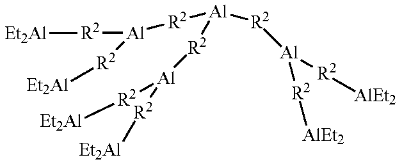 | $[Al][(R^2Al)_2{}^2(Et)]_3$ |
| 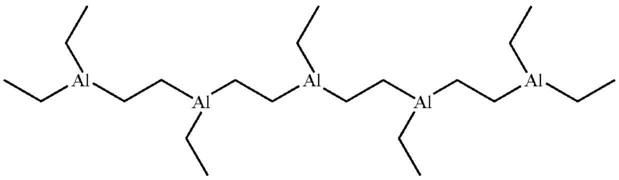 | $[AlEt][(CH_2CH_2AlEt)_1{}^2(Et)]_2$ |
| 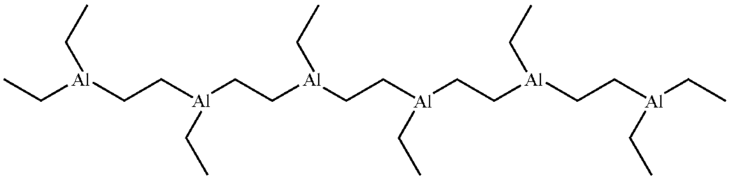 | $[EtAl(CH_2)_2AlEt][(CH_2CH_2AlEt)_1{}^2(Et)]_2$ |

An additional aspect of this disclosure provides for chain shuttling agents that are not readily described by the Newkome nomenclature, to the extent that they are not formally dendritic species. Specifically, the group 12 reagents $M^C[R^2]_2M^C$, where $M^C$ is Mg, and the group 13 reagents $M^B[R^2]_3M^B$, where $M^B$ is B, Al, or Ga are chain shuttling agents that are useful in the disclosed polymerizations, but are not classic dendrimers. Examples of these species include the following compounds:

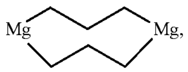, 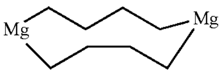,

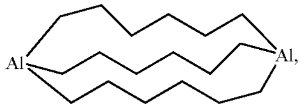,

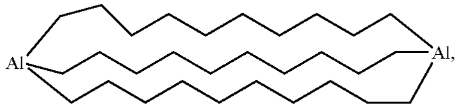, and the like. As provided, these structures are representative of the polymeric species that constitute the CSA compositions of this stoichiometry. Therefore, chain shuttling agents that are encompassed by this disclosure include those having the formula:

$R^1[M^A\text{-}R^2—]_N M^A R^1$, wherein $M^A$ is Zn or Mg, $R^1[M^B\text{-}R^2—]_N M^B(R^1)_2$, wherein $M^B$ is B, Al, or Ga, or $M^C[R^2]_2M^C$, wherein $M^C$ is Mg, $M^B[R^2]_3M^B$, wherein $M^B$ is B, Al, or Ga;

or an aggregate thereof, a Lewis base-containing derivative thereof, or any combination thereof; wherein $R^1$ in each occurrence is independently a monovalent group such as hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 30 carbon atoms;

$R^2$ in each occurrence is independently selected from $(CH_2)_m$, $O[(CH_2)_nCH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]$, $(R^B)_3SiOSiR^B[(CH_2)_nCH_2CH_2]$, or $[Si(R^B)_2(CH_2)_nCH_2CH_2]_2O$; wherein n in each occurrence is independently an integer from 1 to 20, inclusive; m is an integer from 2 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

A further aspect of the chain shuttling agents of this disclosure is provided by considering the parameter Q, as defined above. When CSAs are used that have the ratio of multi-headed site valencies to mono-headed site valencies, Q, to values greater than one (Q>1), then co-polymers or interpolymers having more desirable polymer properties, such as a more narrow molecular weight distribution as compared to polymers resulting from chain shuttling agents without such limits can be prepared. Thus, one aspect of this disclosure is the use of chain shuttling agents with 2 or more metal atoms per CSA molecule having at least two reactive fragments with valence of two or more, such as $R_2$, $R_3$, $R_4$, and so forth. Compositions, reagents, and methods that involve or comprise any aspect of chain shuttling agents with Q>1 are also encompassed in this disclosure. As used herein, the definition of Q is not limited to alkyl $R^1$ groups, but includes any of the hydrogen, halide, amide, hydrocarbyl, hydrocarbylamide, hydrocarbyloxide, moieties and the like, each of which comprises a mono-headed site valency.

By way of example, the following table includes a variety of dual-headed and multi-headed CSAs that are encompassed by this disclosure and that are useful in the polymerization chemistry described here.

TABLE 2

Examples of Useful Chain Shuttling Agents Encompassed by this Disclosure.

| CSA | R3 | R2 | R1 | Q (>1) |
|---|---|---|---|---|
| $R^1$—[Zn—$R^2$—]$_{N>1}$Zn—$R^1$ | 0 | 2N | 2 | N (>1) |
| 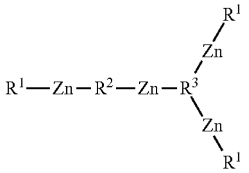 | 3 | 2 | 3 | 5/3 |
| 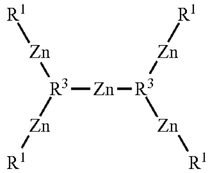 | 6 | 0 | 4 | 3/2 |
| 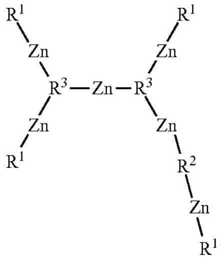 | 6 | 2 | 4 | 2 |
| 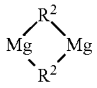 | 0 | 4 | 0 | 4/0 = ∞ |
| 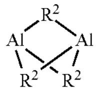 | 0 | 6 | 0 | 6/0 = ∞ |

While the CSAs of this disclosure typically have Q>1, one type of CSA that is encompassed herein can have a Q as low as 4/5. Specifically, this exceptional CSA is the linear, group 13 (B, Al, Ga) chain shuttling agents having the formula $R^1[M^B\text{-}R^1—R^2—]_{N>1}M^BR^1_2$, where $M^B$ is B, Al, or Ga. By referring to the CSAs of this disclosure as having Q>1, it is intended to include this exception for the group 13 CSAs of the form $R^1[M^B\text{-}R^1—R^2—]_{N>1}M^BR^1_2$ that have a Q as low as 4/5. When these CSAs are the linear reagents rather than the branched reagents, useful CSAs of this disclosure include those $R^1[M^B\text{-}R^1—R^2—]_{N>1}M^BR^1_2$ compounds having at least three Group 13 atoms, that is, $R^1[M^B\text{-}R^1—R^2—]_2M^BR^1_2$, $R^1[M^BR^1—R^2—]_3M^BR^1_2$, $R^1[M^BR^1—R^2—]_4M^BR^1_2$, and larger, although the smallest molecule having N=2, provides a calculated Q of less than 1. Nonetheless, all of these linear, group 13 reagents are included here as long as N>1. To illustrate group 13 CSAs of the form $R^1[M^BR^1—R^2—]_{N>1}M^BR^1_2$ and their calculated Q values, in the CSA $R^1[M^BR^1—R^2—]_{N>1}M^BR^1_2$, the value of R2 is 2N, and the value of R1 is 3+N. Therefore, when N is 2, for the smallest CSA of this formula with N>1, then Q(=R2/R1) is 4/5. Larger CSAs of this formula have calculated Q values>1; for example, when N=3, Q=8/7, and when N=4, Q=10/8.

A further aspect of this disclosure provides for a catalyst composition comprising the contact product at least one polymerization catalyst precursor, at least one cocatalyst, and at least one shuttling agent having the formula $R^1[M^A\text{-}R^2—]_N M^AR^1$, $R^1[M^BR^1—R^2—]_NM^B(R^1)_2$, $M^C[R^2]_2M^C$, or $M^B[R^2]_3M^B$, or an aggregate thereof, a Lewis base-containing derivative thereof, or any combination thereof; wherein each variable $M^A$, $M^B$, $M^C$, $R^1$, $R^2$, x and N are defined herein.

Considering the general formulas of the chain shuttling agents $R^1[M^A\text{-}R^2—]_NM^AR^1$, $R^1[M^BR^1—R^2—]_NM^B(R^1)_2$, $M^C[R^2]_2M^C$, or $M^B[R^2]_3M^B$, certain selections of $R^1$, $R^2$, and N can be particularly useful. In this aspect, for example, values of N can be 2, 3, 4, 5, 6, 7, 8, 9, 10, 11, 12, 13, 14, 15, 16, 17, 18, 19, or values of about 20, 25, 30, 35, 40, 45, 50, 55, 60, 65, 70, 75, 80, 85, 90, 95, 100, 110, 120, 130, 140, or 150, or even greater, including any range or set of ranges between any of these values. Any particular sample of $R^1[M^A\text{-}R^2—]_N M^AR^1$ and $R^1[M^BR^1—R^2—]_NM^B(R^1)_2$ is expected to contain a mixture of different species having different N values, therefore, any given sample of these CSAs will be characterized by having a range of values of N. Formulas such as $R^1[M^A\text{-}R^2—]_NM^AR^1$ and $R^1[M^BR^1—R^2—]_NM^B(R^1)_2$ as used in this disclosure are intended to reflect a population of molecules, characterized by a range or distribution of N values. Therefore, unless provided otherwise, values of N are stated as average values for the mixture of species in a particular sample, as evidenced by the ratio of $R^2$ to $R^1$ moieties which can be determined by, for example, $^1$H NMR.

Within the general CSA formulas provided here, any number of useful $R^2$ moieties can be used. As used herein, $R^2$ is any moiety with two site valencies, that does not prevent the formation and chain-shuttling activity of the chain shuttling agent that contains that specific $R^2$. Desirably, the specific $R^2$ does not contain a reactive functional group or reactive moiety that substantially adversely reacts with or interferes with a borohydride or an alkylzinc reagent. The typical example of an $R^2$ is a hydrocarbdiyl, such as alkdiyl. For example, as illustrated in the schemes and examples, $R^2$ can be derived from an α,ω-diene-containing species, including α,ω-dienes (also termed α,ω-diolefins), and therefore $R^2$ can be defined according to the α,ω-diene-containing precursor used in its preparation. As used here, the term "α,ω-diene" is used interchangeably with "α,ω-diene-containing" molecules or species to refer to any compound that contains at least two terminal olefin moieties ($—CH{=}CH_2$), and are not intended to be limiting to strictly hydrocarbon species. The synthetic method for preparing the dual-headed zinc reagents described in the examples generally are applicable to the synthesis of any chain shuttling agent derived from any α,ω-diene-containing species, or any molecule that contains multiple olefin groups. These precursors are selected such that the diene does not contain a reactive functional group, which can adversely react with or interfere with a borohydride or an alkylzinc reagent. In appropriate cases, molecules that contain multiple olefin groups and functional groups that have been suitably protected as understood by one skilled in the art, can be used if it interferes with a borohydride or an alkylzinc reagent. Generally, the suitable $R^2$ groups can have from 2 to 40 carbon atoms, inclusive. The $R^2$ groups can have up from 2 to 25 carbon atoms, from 2 to 15 carbon atoms, or from 2 to 12 carbon atoms, inclusive.

Examples of suitable α,ω-diene-containing species include hydrocarbyl α,ω-dienes, functionalized hydrocarbyl α,ω-dienes such as heteroatom-functionalized diene compounds, and other α,ω-diene-containing compounds such as 1,3-di(ω-alkenyl)-tetramethyldisiloxanes and di(ω-alkenyl) ethers. The corresponding $R^2$ moieties that arise from use of these α,ω-diene-containing compounds include the corresponding alkdiyl-type moiety arising from addition to the specific α,ω-diene-containing compounds noted; however, this disclosure encompasses such corresponding $R^2$ moieties, regardless of the particular synthetic method by which the $R^2$ linker might be prepared.

Suitable hydrocarbyl α,ω-dienes as referred to herein include α,ω-dienes having the formula $CH_2{=}CH(CH_2)_nCH{=}CH_2$, where n is an integer from 0 to 20, preferably n is an integer from 1 to 20, including cyclic and bicyclic analogs thereof. Examples of these hydrocarbyl α,ω-dienes include but are not limited to 1,3-butadiene, 1,4-pentadiene, 1,5-hexadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, vinyl norbornene, norbornadiene, dicyclopentadiene, cyclooctadiene, vinyl cyclohexene, and the like, typically containing from 5 to 40 carbon atoms. Accordingly, the $R^2$ moieties that arise from use of these α,ω-diene-containing precursors include the corresponding alkdiyl moiety arising from addition to the named diene, having the formula $[—CH_2CH_2(CH_2)_nCH_2CH_2—]$ where n is an integer from 1 to 20. For example, the $R^2$ moieties that are derived from the dienes listed above would include 1,5-pentdiyl (arising from 1,4-pentadiene), 1,6-hexdiyl (arising from 1,5-hexadiene), 1,7-heptdiyl (arising from 1,6-heptadiene), and so forth. While ethandiyl (or ethdiyl) ($C_2$) and 1,3-propdiyl ($C_3$) linkers are also useful in the chain shuttling agents of this disclosure, CSAs containing these molecules typically are prepared by a different route than the method of Scheme 3, as described in the Examples section of the present disclosure, that is useful for these longer α,ω-diene precursors. Ethandiyl could be prepared by a known procedure (Eisch, J. J.; Kotowicz, B. W. Eur. *J. Inorg. Chem.* 1998, 761-769). Linkers of C3 are prepared by a known route (Bhanu Prasad, A. S.; Eick, H.; Knochel, P. J. *Organomet. Chem.* 1998, 562, 133-139.). Moreover, the 1,4-butdiyl ($C_4$) CSA linkers generally are prepared by routes similar to those for propandiyl.

Functionalized hydrocarbyl α,ω-dienes as referred to herein include α,ω-dienes which are heteroatom-substituted by at least one O, S, N, or Si atom, or a combination of atoms. Specific examples of functionalized hydrocarbyl α,ω-dienes include but are not limited to compounds having the formulas $O[(CH_2)_nCH{=}CH_2]_2$, $S[(CH_2)_nCH{=}CH_2]_2$, $R^A[(CH_2)_nCH{=}CH_2]_2$, $(R^B)_2Si[(CH_2)_nCH{=}CH_2]_2$, $(R^B)_3SiOSiR^B[(CH_2)_nCH{=}CH_2]_2$, and $[Si(R^B)_2(CH_2)_nCH{=}CH_2]_2O$; wherein n in each occurrence is independently an integer from 0 to 20, inclusive, preferably 1 to 20 inclusive; $R^A$ is H or a hydrocarbyl having from 1 to 12 carbon atoms, inclusive; and , $R^B$ in each occurrence is independently a hydrocarbyl having from 1 to 12 carbon atoms, inclusive. Accordingly, the $R^2$ moieties that arise from use of these α,ω-diene-containing compounds include the corresponding alkdiyl-type moiety arising from addition to the specific α,ω-diene-containing compounds noted, and this disclosure encompasses such $R^2$ moieties, independent of any particular synthetic method by which they are prepared. For example, the $R^2$ moieties that are derived from $O[(CH_2)_nCH{=}CH_2]_2$ and their corresponding $O[(CH_2)_nCH_2CH_2—]_2$ moieties are included.

Examples of functionalized hydrocarbyl α,ω-dienes include but are not limited to divinyl ether, di(2-propenyl) ether, di(3-butenyl)ether, di(4-pentenyl)ether, di(5-hexenyl) ether, divinyl amine, di(2-propenyl)amine, di(3-butenyl)

amine, di(4-pentenyl)amine, di(5-hexenyl)amine, divinyl methylamine, di(2-propenyl)methylamine, di(3-butenyl)methylamine, di(4-pentenyl)methylamine, di(5-hexenyl)methylamine, divinyl thioether, di(2-propenyl)thioether), di(3-butenyl)thioether, di(4-pentenyl)thioether, di(5-hexenyl) thioether, divinyl dimethylsilane, di(2-propenyl) dimethylsilane, di(3-butenyl)dimethylsilane, di(4-pentenyl) dimethylsilane, di(5-hexenyl)dimethylsilane, and the like, typically containing from 4 to 40 carbon atoms.

Further examples of suitable functionalized hydrocarbyl α,ω-dienes include but are not limited to the disiloxane compounds such as the 1,1- and the 1,3-isomers of divinyl tetramethyldisiloxane (also referred to here as di(ethan-1,2-diyl) tetramethyldisiloxane), di(2-propenyl) tetramethyldisiloxane, di(3-butenyl)tetramethyldisiloxane, di(4-pentenyl)tetramethyldisiloxane, di(5-hexenyl)tetramethyldisiloxane, di(6-heptenyl)tetramethyldisiloxane, di(7-octenyl)tetramethyldisiloxane, di(8-nonenyl)tetramethyldisiloxane, di(9-decenyl)-tetramethyldisiloxane, divinyltetraethyldisiloxane, di(2-propenyl)tetraethyldisiloxane, di(3-butenyl)tetraethyldisiloxane, di(4-pentenyl)tetraethyldisiloxane, di(5-hexenyl)-tetraethyldisiloxane, di(6-heptenyl)tetraethyldisiloxane, di(7-octenyl) tetraethyldisiloxane, di(8-nonenyl)tetraethyldisiloxane, di(9-decenyl)tetraethyldisiloxane, and the like. The respective $R^2$ moieties that would arise from these precursors are the 1,1- and the 1,3-isomers of di(ethan-1,2-diyl)tetramethyldisiloxane, di(propan-1,3-diyl)tetramethyldisiloxane, di(butan-1,4-diyl)tetramethyldisiloxane, di(pentan-1,5-diyl)tetramethyldisiloxane, di(hexan-1,6-diyl)tetramethyldisiloxane, di(heptan-1,7-diyl)tetramethyldisiloxane, di(octan-1,8-diyl) tetramethyldisiloxane, di(non-1,9-diyl)tetramethyldisiloxane, di(decan-1,10-diyl)tetramethyldisiloxane, di(ethan-1,2-diyl)tetraethyldisiloxane, di(propan-1,3-diyl) tetraethyldisiloxane, di(butan-1,4-diyl)tetraethyldisiloxane, di(pentan-1,5-diyl)tetraethyldisiloxane, di(hexan-1,6-diyl) tetraethyldisiloxane, di(heptan-1,7-diyl)tetraethyldisiloxane, di(octan-1,8-diyl)tetraethyldisiloxane, di(non-1,9-diyl)tetraethyldisiloxane, and di(decan-1,10-diyl)-tetraethyldisiloxane. Generally, the suitable 1,1- and 1,3-di(ω-alkenyl)-tetraalkyldisiloxane type $R^2$ moieties can have from 8 to 40 carbon atoms, inclusive, or from 8 to 30 carbon atoms, or from 8 to 20 carbon atoms.

In this aspect, it is noted that unsymmetric α,ω-diene-containing molecules can be employed, examples of which include (3-butenyl)(5-hexenyl)ether, (2-propenyl)(4-pentenyl)ethylamine, and so forth. These functionalized hydrocarbyl α,ω-diene precursors also give rise to the corresponding alkdiyl-type moiety arising from addition to the named diene. For example, di(3-butenyl)ether would form the corresponding $R^2$ di(butdiyl)ether linker illustrated below.

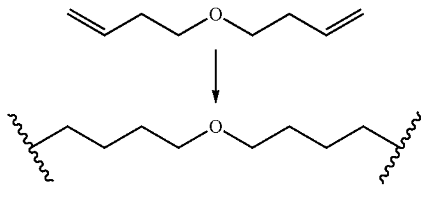

All the α,ω-diene-containing species disclosed here provide the corresponding alkdiyl-type moiety upon addition to the named diene, for example, the 1,3-dialkdiyltetralkyldisiloxane that corresponds to the 1,3-di(ω-alkenyl)tetraalkyldisiloxane employed.

This disclosure also provides for methods of making the novel chain shuttling agents. For example, a process is provided for preparing a chain shuttling agent having the formula:

$R^1[M^A\text{-}R^2—]_N M^A R^1$, wherein $M^A$ is Zn or Mg, or $R^1[M^B R^1—R^2—]_N M^B(R^1)_2$, wherein $M^B$ is B, Al, or Ga;

or an aggregate thereof, a Lewis base-containing derivative thereof, or any combination thereof; the process comprising:

providing an α,ω-diene having the formula $CH_2=CH(CH_2)_nCH=CH_2$, $O[(CH_2)_nCH=CH_2]_2$, $S[(CH_2)_nCH=CH_2]_2$, $R^AN[(CH_2)_nCH=CH_2]_2$, $(R^B)_2Si[(CH_2)_nCH=CH_2]_2$, $(R^B)_3SiOSiR^B[(CH_2)_nCH=CH_2]_2$, or $[Si(R^B)_2(CH_2)_nCH=CH_2]_2O$; wherein n in each occurrence is independently an integer from 0 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive;

contacting the α,ω-diene with a borohydride compound having the formula $(R^C)_2BH$, wherein $R^C$ is a hydrocarbyl having from 1 to 20 carbon atoms, to form a first composition; and contacting the first composition with $M^A(R^{1A})(R^1)$ or $M^B(R^{1A})(R^1)_2$ to form a second composition comprising the chain shuttling agent;

wherein $R^{1A}$ in each occurrence is independently selected from hydrogen or a hydrocarbyl having from 1 to 20 carbon atoms, inclusive, optionally substituted with at least one halide, amide, hydrocarbylamide, dihydrocarbylamide, or hydrocarbyloxide;

$R^1$ in each occurrence is independently selected from hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 20 carbon atoms, inclusive;

$R^2$ in each occurrence is independently selected from $(CH_2)_m$, $O[(CH_2)_nCH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]_2$, $(R^B)_3SiOSiR^B[(CH_2)_nCH_2CH_2]_2$, or $[Si(R^B)_2(CH_2)_nCH_2CH_2]_2O$; wherein n in each occurrence is independently an integer from 1 to 20, inclusive; m is an integer from 2 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

The average value of N can be controlled by adjusting the relative amount of $M^A(R^{1A})(R^1)$ or $M^B(R^{1A})(R^1)_2$ relative to the calculated amount of α,ω-diene or $(R^C)_2BH$ in the second composition.

Similarly, also provided is a process for preparing a chain shuttling agent having the formula:

$R^{1B}[M^A\text{-}R^2—]_N M^A R^{1B}$, wherein $M^A$ is Zn or Mg, or $R^{1B}[M^B R^1—R^2—]_N M^B(R^{1B})_2$, wherein $M^B$ is B, Al, or Ga;

or an aggregate thereof, a Lewis base-containing derivative thereof, or any combination thereof; the process comprising contacting the CSAs of the formula:

$R^{1A}[M^A\text{-}R^2—]_N M^A R^{1A}$ or $R^{1A}[M^B R^{1A}—R^2—]_N M^B(R^{1A})_2$, wherein $R^{1A}$ in each occurrence is independently selected from hydrogen or a hydrocarbyl having from 1 to 20 carbon atoms, inclusive, optionally substituted with at least one halide, amide, hydrocarbylamide, dihydrocarbylamide, or hydrocarbyloxide; and with $HR^{1B}$ to provide a $R^{1B}[M^A\text{-}R^2—]_N M^A R^{1B}$ or $R^{1B}[M^B R^{1B}—R^2—]_N M^B(R^{1B})_2$; or wherein $R^{1B}$ in each occurrence is independently selected from halide, amide, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^{1B}$ having from 1 to 20 carbon atoms, inclusive;

In this embodiment, $R^2$ and N are as provided above for the CSAs $R^1[M^A\text{-}R^2—]_N M^A R^1$ and $R^1[M^B R^1—R^2—]_N M^B(R^1)_2$. The average value of N can be controlled here also by adjusting the relative amount of $M^A(R^{1A})_2$ or $M^B(R^{1A})_3$ relative to the calculated amount of α,ω-diene or $(R^C)_2BH$ in the second composition.

The chain shuttling agents $M^C[R^2]_2M^C$, where $M^C$ is Mg and $M^B[R^2]_3M^B$, where $M^B$ is B, Al, or Ga, can be prepared by providing an α,ω-diene such as disclosed herein, and contacting the α,ω-diene with a composition that serves as a precursor of $M^CH_2$ or $M^BH_3$, an example of which is triisobutyl aluminum or diisobutyl aluminum hydride.

As illustrated in the examples, other methods for the preparation of CSAs are provided For example, $R^1[M^A\text{-}R^2—]_N M^A R^1$ where $M^A$ is Zn or Mg, can be prepared by reacting a chain shuttling agent of the formula $M^A[R^2]_2M^A$ with a reagent having the formula $R^1[M^A\text{-}R^2—]M^A R^1$. That is, the $R^1[M^A\text{-}R^2—]M^A R^1$ is a dual headed CSA similar to those of formula $R^1[M^A\text{-}R^2—]_N M^A R^1$ provided here, except where the value of N is 1. Similarly, chain shuttling agents having the formula $R^1[M^B R^1—R^2—]_N M^B(R^1)_2$, where $M^B$ is B, Al, or Ga, can be prepared by contacting a chain shuttling agent having the formula $M^B[R^2]_3M^B$ with a reagent having the formula $R^1[M^B R^1—R^2—]M^B(R^1)_2$, where $R^1[M^B R^1—R^2—]M^B(R^1)_2$ is also similar to those of $R^1[M^B R^1—R^2—]_N M^B(R^1)_2$ disclosed here, except with the value of N equal to 1.

Methods for preparing a chain shuttling agent represented by the following Newkome dendrimer nomenclature $[C][(R)N^G{}_b(Z)]N_c$ are also provided. For example, in one apsect, dendrimer CSAs can be prepared as follows, as illustrated in Schemes 8 and 9.

Providing a polyene having the formula $R^AC[(CH_2)_nCH{=}CH_2]_3$ or $C[(CH_2)_nCH{=}CH_2]_4$, wherein n in each occurrence is independently an integer from 0 to 20 and $R^A$ is H or a hydrocarbyl having from 1 to 12 carbon atoms, inclusive; and contacting the polyene with a borohydride having the formula $(R^C)_2BH$, wherein $R^C$ is a hydrocarbyl having from 1 to 20 carbon atoms, to form a first composition comprising a partially hydroborated polyene;

contacting the first composition with $M^A(R^{1A})_2$ or $M^B(R^{1A})_3$ to form a second composition, comprising $M^A\{CH_2CH_2(CH_2)_nE[(CH_2)_nCH{=}CH_2]_{m-1}\}_2$ or $M^B\{CH_2CH_2(CH_2)_nE[(CH_2)_nCH{=}CH_2]_{m-1}\}_3$, wherein $R^{1A}$ in each occurrence is independently a hydrocarbyl having from 1 to 20 carbon atoms, inclusive, optionally substituted with at least one halide, amide, hydrocarbylamide, dihydrocarbylamide, or hydrocarbyloxide;

contacting the second composition with $(R^C)_2BH$, followed by contacting the resulting composition with $M^A(R^{1A})_2$ or $M^B(R^{1A})_3$ to form a third composition;

contacting the third composition with a partially hydroborated polyene prepared according to step b); and repeating steps d) and e) any number of times to form a dendrimeric chain shuttling agent.

In one aspect, the block copolymers provided by the methods and CSAs of this disclosure can be characterized by relatively narrow molecular weight distributions. For example, polymers having a narrow molecular weight distribution typically have a polydispersity index (PDI=Mw/Mn) of from 1.0 to 4.0, more generally from 1.05 to 3.5, or from 1.1 to 2.5. In contrast, polymers generally considered as having broad PDI include those with PDIs from 4.0 to 20 or from 4.0 to 10.

In one aspect, this disclosure encompasses dual-headed chain shuttling agents having the formula $R^1[M^A\text{-}R^2—]_N M^A R^1$, $R^1[M^B R^1—R^2—]_N M^B(R^1)_2$, $M^C[R^2]_2M^C$, and $M^B[R^2]_3M^B$, where $R^1$ and $R^2$ are defined as disclosed herein, and N in each occurrence can be an integer from 2 to 150, inclusive. Thus, examples of chain shuttling agents encompassed by this disclosure include those with N>1 in these formulas. As values of N increase, the ratio (Q) of multi-headed CSA sites (for example, alkdiyl or $R^2$) to mono-headed CSA sites (for example, alkyl or $R^1$) also increases, and the resulting polymer composition properties can be altered, as provided in Table 6. For example, the polydispersity of the resulting ethylene copolymers prepared using increasingly longer dual-headed CSAs is shown to decrease as Q increases. Thus, as the value of Q increases, the overall molecular weight increases while polydispersity decreases and approach the values for the dual headed CSA, calculated as having a PDI of 1.5. The following structure illustrates the difference between a dual-headed CSA site (D) which constitutes each alkandiyl zinc bond and a mono-headed CSA site (M) which constitutes each alkyl zinc bond. For CSAs of the formulas $R^1[M^A\text{-}R^2—]_N M^A R^1$, $R^1[M^B R^1—R^2—]_N\text{-}M^B(R^1)_2$, $M^C[R^2]_2M^C$, and $M^B[R^2]_3M^B$, the multi-headed CSA sites are all alkdiyl or $R^2$ sites, therefore Q is the ratio of dual-headed (D) to mono-headed (M) sites.

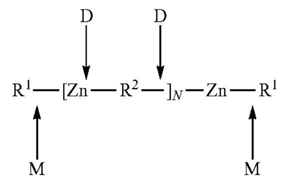

While not intending to be bound by theory, it is thought that the dual-headed CSAs of this disclosure, for example compounds of the formulas $R^1—[Zn—R^2—]_N Zn—R^1$ and $R^1—[AlR^1—R^2—]_N AlR^1{}_2$ where Q, the ratio of $R^2$ sites (two per $R^2$) to $R^1$ sites (one per $R^1$), is greater than 1, form mostly odd-numbered multi-block polymers. Again, while not theory-bound, this feature is thought to affect the polymer distribution such that it is not multimodal, and will have a narrower molecular weight distribution than polymers using dual headed CSAs of the formulas $R^1[M^A\text{-}R^2—]_N M^A R^1$ and $R^1[M^B R^1—R^2—]_N M^B(R^1)_2$, where the ratio of $R^2$ sites to $R^1$ sites, Q is equal to 1.

As provided here, the dual-headed chain shuttling agents of the formulas $R^1[M^A\text{-}R^2—]_N M^A R^1$ and $R^1[M^B R^1—R^2—]_N M^B(R^1)_2$ are characterized by having values of N>1. In one aspect, the rapid room temperature exchange of zinc-hydrocarbyl groups between and among dihydrocarbyl zinc molecules can be used to adjust the value or range of values of N in the chain shuttling agents when M is zinc. This rapid and reversible equilibrium aspect is used to synthetic advantage here, for example, as illustrated in Scheme 1, where a solution of $Et[ZnCH_2CH_2]ZnEt$ establishes an equilibrium and generates a solution containing an approximately statistical mixture of $Et[ZnCH_2CH_2]_2ZnEt$ and $ZnEt_2$. Similarly, Scheme 2 illustrates how $Et[ZnCH_2CH_2]_2ZnEt$ in solution can set up further equilibria, for example, with another molecule of $Et[ZnCH_2CH_2]_2ZnEt$ to form $Et[ZnCH_2CH_2]_5ZnEt$ and $ZnEt_2$. These reactions are reversible; therefore, the value of N can be lowered by combining a known amount of $ZnR^1_2$ such as a dialkyl zinc, with a known amount of the dual-headed CSA. Similarly, the value of N can be increased by dissolving the dual headed zinc chain shuttling agent in a solvent such as toluene and placing the solution under vacuum. In this latter case, the more volatile $ZnR^1_2$, for example $ZnEt_2$, is removed by vacuum, driving the equilibrium away from lower values of N toward higher N values.

The ratio of $R^2$ to $R^1$ moieties can be measured by $^1H$ NMR and $^{13}C\{^1H\}$ NMR spectroscopy and used to determine the average value or range of values of N for the $Et[ZnCH_2CH_2]_N ZnEt$ prepared in this manner.

Scheme 1

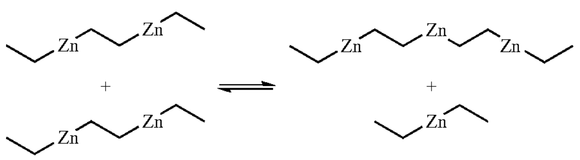

The various chain shuttling and polymerization steps that can occur using such CSAs can be understood by reference to WO 2007/035493, which is incorporated herein by reference in its entirety. The skilled artisan will appreciate that the various steps illustrated in WO 2007/035493 and as disclosed here may occur in any order. For example, by selecting different catalysts with respect to their ability or inability to incorporate comonomer, or otherwise produce distinguishable polymers, the polymer segments formed by the respective catalysts, will possess distinct physical properties. In particular, in one embodiment, a block copolymer having at least one block of a highly crystalline ethylene or propylene polymer characterized by little or no comonomer incorporation and at least one other block of an amorphous ethylene or propylene copolymer characterized by a greater quantity of comonomer incorporation, may be readily prepared in this manner. The skilled artisan will appreciate that by employing multiple catalysts, multiple monomers, multiple chain shuttling agents (including both dual-headed and multi-headed types), multiple reactors, or variable reactor conditions, a large number of combinations of reaction products are attainable.

The polymer product provided here may be recovered by termination, such as by reaction with water or another proton source, or functionalized, if desired, forming vinyl, hydroxyl, silane, carboxylic acid, carboxylic acid ester, ionomeric, or other functional terminal groups, especially to replace the chain shuttling agent. Alternatively, the polymer segments may be coupled with a polyfunctional coupling agent, especially a difunctional coupling agent such as tolyl diisocyanate, dichlorodimethylsilane or ethylenedichloride, and recovered.

Scheme 2

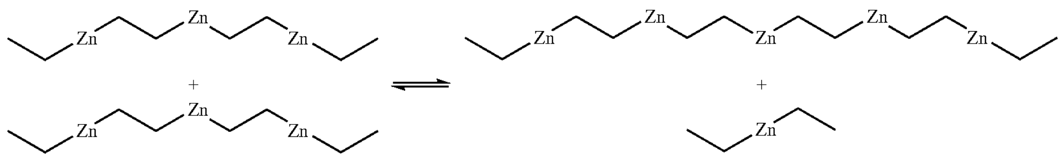

The dual-headed chain shuttling agents of the formulas $R^1[Zn—R^2—]_N ZnR^1$, $R^1[Mg—R^2—]_N MgR^1$, $R^1[BR^1—R^2—]_N B(R^1)_2$, $R^1[AlR^1—R^2—]_N Al(R^1)_2$, and $R^1[GaR^1—R^2—]_N Ga(R^1)_2$, can be prepared according to Examples 1 and 2. Reagent selection allows variation in $R^1$ and $R^2$, while variables such as stoichiometry of the $(R^1)_2M^A$ or $(R^1)_3M^B$ to $\alpha,\omega$-$Et_2B(CH_2)_nBEt_2$, solvent selection, the temperature and reaction time, and the like, allow adjustment of the approximate values of N in the listed formulas. For example, by controlling the molar ratio of $(R^1)_2M^A$ or $(R^1)_3M^B$ to $\alpha,\omega$-$Et_2B(CH_2)_nBEt_2$ such that there is less than a 10-fold excess of either organometal reagent ($(R^1)_2M^A$ or $(R^1)_3M^B$) and less than a 10-fold excess of $\alpha,\omega$-$Et_2B(CH_2)_nBEt_2$ reagent can provide the desired dual-headed chain shuttling agents having values of N greater than 1. In another aspect, controlling the stoichiometry such that there is less than a 5-fold excess of either organometal reagent ($(R^1)_2M^A$ or $(R^1)_3M^B$) and less than a 5-fold excess of $\alpha,\omega$-$Et_2B(CH_2)_nBEt_2$ reagent can provide DH CSAs with values of N greater than 1. Further, the DH CSAs with values of N greater than 1 can be prepared when the molar ratio of organometal reagent ($(R^1)_2M^A$ or $(R^1)_3M^B$) to $\alpha,\omega$-$Et_2B(CH_2)_nBEt_2$ reagent is from about 7:1 to about 0.5:1, from about 5:1 to about 1:1, or from about 4:1 to about 2:1.

The skilled artisan will readily appreciate that the foregoing process may employ a multi-centered dendritic shuttling agent initially containing 2, 3, 4 or even more active centers, resulting in the formation of polymer mixtures containing some quantity of a polymer that has approximately double, triple, quadruple, or other multiple of the molecular weight of the remaining polymer and a star or branched morphology, before hydrolysis.

In one aspect of this disclosure, the rate of chain shuttling is equivalent to or faster than the rate of polymer termination, for example, up to 10 times faster, or even up to 100 times faster or more, than the rate of polymer termination and significant with respect to the rate of polymerization. This permits formation of significant quantities of polymer chains terminated with chain shuttling agents and capable of continued monomer insertion leading to significant quantities of the higher molecular weight polymer.

By selecting different shuttling agents or mixtures of agents with a catalyst, by altering the comonomer composition, temperature, pressure, optional chain transfer agent such as $H_2$, or other reaction conditions in separate reactors or zones of a reactor operating under plug flow conditions, polymer products having segments of varying density or comonomer concentration, monomer content, and/or other distinguishing property can be prepared. For example, in a typical process employing two continuous solution polymerization reactors connected in series and operating under differing polymerization conditions, the resulting polymer segments will each have a most probable molecular weight distribution characteristic of typical olefin coordination polymerization catalysts, but will reflect the differing polymerization conditions of their formation. In addition, certain quantities of a conventional random copolymer may also be formed coincident with formation of the present polymer composition, resulting in a resin blend. If a relatively fast shuttling agent is employed, a copolymer having shorter block lengths but more uniform composition is obtained, with little formation of random copolymer. By proper selection of both catalyst and multi-centered shuttling agent, relatively pure mixtures of two polymers differing in molecular weight by approximately an integer value, copolymers containing relatively large polymer segments or blocks approximating true block copolymers, or blends of the foregoing with more random copolymers can all be obtained.

In a further aspect of this disclosure, single-headed chain shuttling agents may be employed in combination with the dual-headed or multi-headed shuttling agents disclosed herein. In this aspect, suitable single-headed chain shuttling agents include metal compounds or complexes of metals of Groups 1-13, preferably Group 1, 2, 12 or 13 of the Periodic Table of the Elements. While not limited by hydrocarbyl size, suitable single-headed CSAs usually include hydrocarbyl substituted aluminum, gallium or zinc compounds containing from 1 to 20 carbons or from 1 to 12 carbons in each hydrocarbyl group, and reaction products thereof with a proton source. Typical hydrocarbyl groups include linear or branched $C_{2-8}$ alkyl groups. In one aspect, the single-headed CSA includes trialkyl aluminum, dialkyl zinc compounds, or combinations thereof, examples of which include triethylaluminum, tri(i-propyl)aluminum, tri(i-butyl)aluminum, tri(n-hexyl)aluminum, tri(n-octyl)aluminum, triethylgallium, or diethylzinc. Additional suitable shuttling agents include the reaction product or mixture formed by combining at least one of the foregoing organometal compounds, for example, a tri($C_{1-8}$)alkyl aluminum or di($C_{1-8}$)alkyl zinc compound such as triethylaluminum, tri(i-propyl)aluminum, tri(i-butyl)aluminum, tri(n-hexyl)aluminum, tri(n-octyl)aluminum, or diethylzinc, with a less than stoichiometric quantity (relative to the number of hydrocarbyl groups) of a secondary amine or a hydroxyl compound, such as bis(trimethylsilyl)amine, t-butyl(dimethyl)siloxane, 2-hydroxymethylpyridine, di(n-pentyl)amine, 2,6-di(t-butyl)phenol, ethyl(1-naphthyl)amine, bis(2,3,6,7-dibenzo-1-azacycloheptaneamine), or 2,6-diphenylphenol. Desirably, sufficient amine or hydroxyl reagent is used such that one hydrocarbyl group remains per metal atom. Examples of the primary reaction products of the foregoing combinations most desired for use in the present disclosure as shuttling agents are n-octylaluminum di(bis(trimethylsilyl)amide), i-propylaluminum bis(dimethyl(t-butyl) siloxide), and n-octylaluminum di(pyridinyl-2-methoxide), i-butylaluminum bis(dimethyl(t-butyl)siloxane), i-butylaluminum bis(di(trimethylsilyl)amide), n-octylaluminum di(pyridine-2-methoxide), i-butylaluminum bis(di(n-pentyl) amide), n-octylaluminum bis(2,6-di-t-butylphenoxide), n-octylaluminum di(ethyl(1-naphthyl)amide), ethylaluminum bis(t-butyldimethylsiloxide), ethylaluminum di(bis(trimethylsilyl)amide), ethylaluminum bis(2,3,6,7-dibenzo-1-azacycloheptaneamide), n-octylaluminum bis(2,3,6,7-dibenzo-1-azacycloheptaneamide), n-octylaluminum bis (dimethyl(t-butyl)siloxide), ethylzinc (2,6-diphenylphenoxide), and ethylzinc (t-butoxide).

The dual-headed chain shuttling agents provided in this disclosure, which include compounds of the general formula $R^1[M^A\text{-}R^2—]_N M^A R^1$ and $R^1[M^B R^1—R^2—]_N M^B(R^1)_2$, where $M^A$ is Zn or Mg and where $M^B$ is B, Al, or Ga, can include a divalent $R^2$ moiety such as a hydrocarbadiyl or a 1,3-dihydrocarbadiyltetralkyldisiloxane groups. In this aspect, $R^2$ can be selected independently from ethandiyl, 1,3-propandiyl, 1,4-butandiyl, 1,5-pentandiyl, 1,6-hexandiyl, 2,5-hexandiyl, 1,7-heptandiyl, 1,8-octandiyl, 1,9-nonandiyl, 1,10-decandiyl, and the like, including larger $R^2$ moieties. Further, $R^2$ also can be selected independently from 1,3-ethandiyl-tetramethyldisiloxane, 1,3-(propan-1,3-diyl)tetramethyldisiloxane, 1,3-(butan-1,4-diyl)tetramethyldisiloxane, 1,3-(pentan-1,5-diyl)tetramethyldisiloxane, 1,3-(hexan-1,6-diyl)tetramethyldisiloxane, 1,3-(heptan-1,7-diyl) tetramethyldisiloxane, 1,3-(octan-1,8-diyl) tetramethyldisiloxane, 1,3-(propan-1,3-diyl) tetraethyldisiloxane, 1,3-(butan-1,4-diyl) tetraethyldisiloxane, 1,3-(pentan-1,5-diyl) tetraethyldisiloxane, 1,3-(hexan-1,6-diyl) tetraethyldisiloxane, 1,3-(heptan-2,7-diyl) tetramethyldisiloxane, 1,3-(octan-1,8-diyl) tetraethyldisiloxane, or similar $R^2$ moieties.

The dual-headed chain shuttling agents provided in this disclosure such as the compounds of the general formula $M^C[R^2]_2M^C$ or $M^B[R^2]_3M^B$, where $M^B$ is B, Al, or Ga, and where $M^C$ is Mg, also can include the divalent $R^2$ moieties such as a hydrocarbadiyl or a 1,3-dihydrocarbadiyltetralkyldisiloxane groups such as those disclosed for the CSAs of the formula $R^1[M^A\text{-}R^2—]_N M^A R^1$ and $R^1[M^B R^1—R^2—]_N M^B(R^1)_2$. In one aspect, CSAs of the general formula $M^C[R^2]_2M^C$ and $M^B[R^2]_3M^B$ typically have $R^2$ moieties selected from the alkdiyl groups such as ethandiyl, 1,3-propandiyl, 1,4-butandiyl, 1,5-pentandiyl, 1,6-hexandiyl, 2,5-hexandiyl, 1,7-heptandiyl, 1,8-octandiyl, 1,9-nonandiyl, 1,10-decandiyl, and the like, or even larger alkdiyl $R^2$ moieties.

Transition Metal Catalyst Precursors

Among other things, this disclosure provides a catalyst composition and various methods that include at least one polymerization catalyst precursor, at least one cocatalyst, and at least one dendritic chain shuttling agent as disclosed herein. Suitable catalysts for use in the methods and compositions disclosed herein include any compound or combination of compounds that is adapted for preparing polymers of the desired composition or type. Both heterogeneous and homogeneous catalysts may be employed. Examples of heterogeneous catalysts include the well known Ziegler-Natta compositions, including the Group 4 metal halides and their derivatives, and including Group 4 metal halides supported on Group 2 metal halides or mixed halides and alkoxides, including the well-known chromium- or vanadium-based catalysts. However, for ease of use and for production of narrow molecular weight polymer segments in solution, especially useful catalysts include the homogeneous catalysts including a relatively pure organometallic compound or metal complex, especially compounds or complexes based on metals selected from Groups 3-15 or the Lanthanide series of the Periodic Table of the Elements.

Suitable catalysts and catalyst precursors for use in the present invention include those disclosed in WO2005/090427, in particular, those disclosed starting on page 25, line 19 through page 55, line 10. Suitable are also disclosed in US 2006/0199930; US 2007/0167578; US 2008/0311812; U.S. Pat. No. 7,355,089 B2; or WO 2009/012215.

One aspect of this disclosure provided for particularly useful polymerization catalyst precursors, including but not limited to those listed as Catalysts A1-A10 in the Examples section of this disclosure as well as any combination thereof.

Catalysts having high comonomer incorporation properties are also known to reincorporate in situ prepared long chain olefins resulting incidentally during the polymerization through β-hydride elimination and chain termination of growing polymer, or other process. The concentration of such long chain olefins is particularly enhanced by use of continuous solution polymerization conditions at high conversions, especially ethylene conversions of 95 percent or greater, and more particularly at ethylene conversions of 97 percent or greater. Under such conditions a small but detectable quantity of vinyl group terminated polymer may be reincorporated into a growing polymer chain, resulting in the formation of long chain branches, that is, branches of a carbon length greater than would result from other deliberately added comonomer. Moreover, such chains reflect the presence of other comonomers in the reaction mixture. That is, the chains may include short chain or long chain branching as well, depending on the comonomer composition of the reaction mixture. However, the presence of an chain shuttling agent during polymerization can seriously limit the incidence of long chain branching since the vast majority of the polymer chains become attached to a CSA species and are prevented from undergoing β-hydride elimination.

Cocatalysts

Each of the metal complexes (also interchangeably referred to here as procatalysts or catalyst precursors) may be activated to form the active catalyst composition by combination with a cocatalyst, preferably a cation forming cocatalyst, a strong Lewis acid, or a combination thereof. Thus, this disclosure also provides for the use of at least one cocatalyst in a catalyst composition and various methods, along with at least one polymerization catalyst precursor, and at least one chain shuttling agent as disclosed herein.

Suitable cation forming cocatalysts include those previously known in the art for metal olefin polymerization complexes. Examples include neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium-, lead- or silver salts of compatible, noncoordinating anions; and combinations of the foregoing cation forming cocatalysts and techniques. The foregoing activating cocatalysts and activating techniques have been previously taught with respect to different metal complexes for olefin polymerizations in the following references: EP-A-277,003; U.S. Pat. Nos. 5,153,157; 5,064,802; 5,321,106; 5,721,185; 5,350,723; 5,425,872; 5,625,087; 5,883,204; 5,919,983; 5,783,512; WO 99/15534, and WO99/42467.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane may be used as activating cocatalysts. Preferred molar ratios of metal complex:tris(pentafluorophenyl-borane:alumoxane are from 1:1:1 to 1:5:20, more preferably from 1:1:1.5 to 1:5:10.

Suitable ion forming compounds useful as cocatalysts in one embodiment of the present disclosure comprise a cation which is a Brønsted acid capable of donating a proton, and a compatible, noncoordinating anion, $A^-$. As used herein, the term "noncoordinating" refers to an anion or substance which either does not coordinate to the Group 4 metal containing precursor complex and the catalytic derivative derived there from, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

In one aspect, suitable cocatalysts may be represented by the following general formula:

$$(L^*-H)AA)_g^+(A)^{g-}, \text{ wherein:}$$

$L^*$ is a neutral Lewis base;

$(L^*-H)^+$ is a conjugate Brønsted acid of $L^*$;

$A^{g-}$ is a noncoordinating, compatible anion having a charge of g−, and g is an integer from 1 to 3.

More particularly, $A^{g-}$ corresponds to the formula: $[MiQ_4]^-$; wherein:

Mi is boron or aluminum in the +3 formal oxidation state; and

Q independently in each occurrence is selected from hydride, dialkyl-amido, halide, hydrocarbyl, hydrocarbyloxide, halosubstituted-hydrocarbyl, halosubstituted hydrocarbyloxy, and halo-substituted silylhydrocarbyl radicals (including perhalogenated hydrocarbyl-perhalogenated hydrocarbyloxy- and perhalogenated silylhydrocarbyl radicals), each Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this disclosure may be represented by the following general formula:

$$(L^*-H)^+(BQ_4)^-; \text{ wherein:}$$

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Especially useful Lewis base salts are ammonium salts, more preferably trialkyl-ammonium salts containing one or more $C_{12-40}$ alkyl groups. In this aspect, for example, Q in each occurrence can be a fluorinated aryl group, especially, a pentafluorophenyl group.

Illustrative, but not limiting, examples of boron compounds which may be used as an activating cocatalyst in the preparation of the improved catalysts of this disclosure include the tri-substituted ammonium salts such as:

trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6 tetrafluorophenyl)borate,
N,N-dimethylanilinium tetrakis(4-(triisopropylsilyl)-2,3,5,6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
dimethyloctadecylammonium tetrakis(pentafluorophenyl)borate,
methyldioctadecylammonium tetrakis(pentafluorophenyl)borate;

a number of dialkyl ammonium salts such as:

di-(i-propyl)ammonium tetrakis(pentafluorophenyl)borate,
methyloctadecylammonium tetrakis(pentafluorophenyl)borate,
methyloctadodecylammonium tetrakis(pentafluorophenyl)borate, and
dioctadecylammonium tetrakis(pentafluorophenyl)borate;

various tri-substituted phosphonium salts such as:

triphenylphosphonium tetrakis(pentafluorophenyl)borate,
methyldioctadecylphosphonium tetrakis(pentafluorophenyl)borate, and
tri(2,6-dimethylphenyl)phosphonium tetrakis(pentafluorophenyl)borate;

di-substituted oxonium salts such as:

diphenyloxonium tetrakis(pentafluorophenyl)borate,
di(o-tolyl)oxonium tetrakis(pentafluorophenyl)borate, and
di(octadecyl)oxonium tetrakis(pentafluorophenyl)borate; and di-substituted sulfonium salts such as:

di(o-tolyl)sulfonium tetrakis(pentafluorophenyl)borate, and
methylcotadecylsulfonium tetrakis(pentafluorophenyl)borate.

Further to this aspect of the disclosure, examples of useful $(L^*-H)^+$cations include, but are not limited to, methyldioctadecylammonium cations, dimethyloctadecylammonium cations, and ammonium cations derived from mixtures of trialkyl amines containing one or two $C_{14-18}$ alkyl groups.

Another suitable ion forming, activating cocatalyst comprises a salt of a cationic oxidizing agent and a noncoordinating, compatible anion represented by the formula:

$(Ox^{h+})_g(A^{g-})_h$, wherein:

$Ox^{h+}$ is a cationic oxidizing agent having a charge of h+;

h is an integer from 1 to 3; and $A^{g-}$ and g are as previously defined.

Examples of cationic oxidizing agents include: ferrocenium, hydrocarbyl-substituted ferrocenium, $Ag^+$, or $Pb^{+2}$. Particularly useful examples of $A^{g-}$ are those anions previously defined with respect to the Bronsted acid containing activating cocatalysts, especially tetrakis(pentafluorophenyl)borate.

Another suitable ion forming, activating cocatalyst can be a compound which is a salt of a carbenium ion and a noncoordinating, compatible anion represented by the following formula:

$[C]^+A^-$ wherein:

$[C]^+$ is a $C_{1-20}$ carbenium ion; and is a noncoordinating, compatible anion having a charge of −1. For example, one carbenium ion that works well is the trityl cation, that is triphenylmethylium.

A further suitable ion forming, activating cocatalyst comprises a compound which is a salt of a silylium ion and a noncoordinating, compatible anion represented by the formula:

$(Q^1{}_3Si)^+A^-$ wherein:

$Q^1$ is $C_{1-10}$ hydrocarbyl, and $A^-$ is as previously defined.

Suitable silylium salt activating cocatalysts include trimethylsilylium tetrakispentafluorophenylborate, triethylsilylium tetrakispentafluorophenylborate, and ether substituted adducts thereof. Silylium salts have been previously generically disclosed in *J. Chem. Soc. Chem. Comm.* 1993, 383-384, as well as in Lambert, J. B., et al., *Organometallics* 1994, 13, 2430-2443. The use of the above silylium salts as activating cocatalysts for addition polymerization catalysts is also described in U.S. Pat. No. 5,625,087.

Certain complexes of alcohols, mercaptans, silanols, and oximes with tris(pentafluorophenyl)borane are also effective catalyst activators and may be used according to the present disclosure. Such cocatalysts are disclosed in U.S. Pat. No. 5,296,433.

Suitable activating cocatalysts for use herein also include polymeric or oligomeric alumoxanes (also called aluminoxanes), especially methylalumoxane (MAO), triisobutyl aluminum modified methylalumoxane (MMAO), or isobutylalumoxane; Lewis acid modified alumoxanes, especially perhalogenated tri(hydrocarbyl)aluminum- or perhalogenated tri(hydrocarbyl)boron modified alumoxanes, having from 1 to 10 carbons in each hydrocarbyl or halogenated hydrocarbyl group, and most especially tris(pentafluorophenyl)borane modified alumoxanes. Such cocatalysts are previously disclosed in U.S. Pat. Nos. 6,214,760, 6,160,146, 6,140,521, and 6,696,379.

A class of cocatalysts comprising non-coordinating anions generically referred to as expanded anions, further disclosed in U.S. Pat. No. 6,395,671, may be suitably employed to activate the metal complexes of the present disclosure for olefin polymerization. Generally, these cocatalysts (illustrated by those having imidazolide, substituted imidazolide, imidazolinide, substituted imidazolinide, benzimidazolide, or substituted benzimidazolide anions) may be depicted as follows:

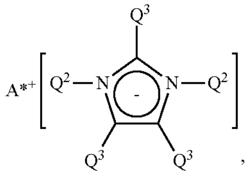

,

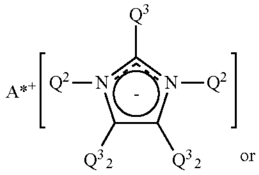

or

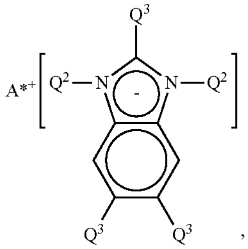

, wherein:

$A^{*+}$ is a cation, especially a proton containing cation, and can be trihydrocarbyl ammonium cation containing one or two $C_{10-40}$ alkyl groups, especially a methyldi($C_{14-20}$ alkyl) ammonium cation, $Q^3$, independently in each occurrence, is hydrogen or a halo, hydrocarbyl, halocarbyl, halohydrocarbyl, silylhydrocarbyl, or silyl, (including for example mono-, di- and tri (hydrocarbyl)silyl) group of up to 30 atoms not counting hydrogen, such as $C_{1-20}$ alkyl, and $Q^2$ is tris(pentafluorophenyl)borane or tris(pentafluorophenyl)alumane).

Examples of these catalyst activators include trihydrocarbylammonium-salts, especially, methyldi($C_{i4-20}$ alkyl)ammonium-salts of:

bis(tris(pentafluorophenyl)borane)imidazolide, bis(tris(pentafluorophenyl)borane)-2-undecylimidazolide, bis(tris(pentafluorophenyl)borane)-2-heptadecylimidazolide, bis(tris(pentafluorophenyl)borane)-4,5-bis(undecyl)imidazolide, bis(tris(pentafluorophenyl)borane)-4,5-bis(heptadecyl) imidazolide, bis(tris(pentafluorophenyl)borane)imidazolinide, bis(tris(pentafluorophenyl)borane)-2-undecylimidazolinide, bis(tris(pentafluorophenyl)borane)-2-heptadecylimidazolinide, bis(tris(pentafluorophenyl)borane)-4,5-bis(undecyl)imidazolinide, bis(tris(pentafluorophenyl)borane)-4,5-bis(heptadecyl) imidazolinide, bis(tris(pentafluorophenyl)borane)-5,6-dimethylbenzimidazolide, bis(tris(pentafluorophenyl)borane)-5,6-bis(undecyl)benzimidazolide, bis(tris(pentafluorophenyl)alumane)imidazolide, bis(tris(pentafluorophenyl)alumane)-2-undecylimidazolide, bis(tris(pentafluorophenyl)alumane)-2-heptadecylimidazolide, bis(tris(pentafluorophenyl)alumane)-4,5-bis(undecyl) imidazolide, bis(tris(pentafluorophenyl)alumane)-4,5-bis(heptadecyl) imidazolide, bis(tris(pentafluorophenyl)alumane)imidazolinide, bis(tris(pentafluorophenyl)alumane)-2-undecylimidazolinide, bis(tris(pentafluorophenyl)alumane)-2-heptadecylimidazolinide, bis(tris(pentafluorophenyl)alumane)-4,5-bis(undecyl) imidazolinide, bis(tris(pentafluorophenyl)alumane)-4,5-bis(heptadecyl) imidazolinide, bis(tris(pentafluorophenyl)alumane)-5,6-dimethylbenzimidazolide, and bis(tris(pentafluorophenyl)alumane)-5,6-bis(undecyl) benzimidazolide.

Other activators include those described in the PCT publication WO 98/07515, such as tris(2,2',2"-nonafluorobiphenyl)fluoroaluminate. Combinations of activators are also contemplated by the disclosure, for example, alumoxanes and ionizing activators in combinations, see for example, EP-A-0 573120, PCT publications WO 94/07928 and WO 95/14044, and U.S. Pat. Nos. 5,153,157 and 5,453,410. For example, and in general terms, WO 98/09996 describes activating catalyst compounds with perchlorates, periodates and iodates, including their hydrates. WO 99/18135 describes the use of organoboroaluminum activators. WO 03/10171 discloses catalyst activators that are adducts of Brønsted acids with Lewis acids. Other activators or methods for activating a catalyst compound are described in, for example, U.S. Pat. Nos. 5,849,852, 5,859,653, and 5,869,723, in EP-A-615981, and in PCT publication WO 98/32775. All of the foregoing catalyst activators as well as any other known activator for transition metal complex catalysts may be employed alone or in combination according to the present disclosure. In one aspect, however, the cocatalyst can be alumoxane-free. In another aspect, for example, the cocatalyst can be free of any specifically-named activator or class of activators as disclosed herein.

In a further aspect, the molar ratio of catalyst/cocatalyst employed generally ranges from 1:10,000 to 100:1, for example, from 1:5000 to 10:1, or from 1:1000 to 1:1. Alumoxane, when used by itself as an activating cocatalyst, can be employed in large quantity, generally at least 100 times the quantity of metal complex on a molar basis.

Tris(pentafluorophenyl)borane, where used as an activating cocatalyst can be employed generally in a molar ratio to the metal complex of from 0.5:1 to 10:1, more preferably from 1:1 to 6:1 most preferably from 1:1 to 5:1. The remaining activating cocatalysts are generally employed in approximately equimolar quantity with the metal complex.

In another aspect, the polymer products can contain at least some quantity of a polymer containing two or more blocks or segments joined by means of a remnant of a dual-headed or multi-headed shuttling agent. Generally the product comprises distinct polymer species having different molecular weights, ideally the larger molecular weights being integer multiples of the smallest. As a general rule, the product comprises a first polymer having a first molecular weight and at least some quantity of a second polymer having a molecular weight that is approximately an integer multiple of the molecular weight of the first polymer, wherein the integer is equal to the number of shuttling centers in the shuttling agent. The polymer recovered from the present process may be terminated to form conventional type polymers, coupled through use of a polyfunctional coupling agent to form multiblock copolymers, including hyper-branched or dendrimeric copolymers, or functionalized by conversion of remnants of the dual-headed or multi-headed shuttling agents into vinyl-, hydroxyl-, amine-, silane, carboxylic acid-, carboxylic acid ester, ionomeric, or other functional groups, according to known techniques.

Polymerization Methods.

In one aspect of this disclosure there is provided a process and the resulting polymer, the process comprising polymerizing one or more olefin monomers in the presence of an olefin polymerization catalyst and a dual-headed or multi-headed shuttling agent (CSA or MSA) in a polymerization reactor or zone thereby causing the formation of at least some quantity of a polymer joined with the remnant of the dual-headed or multi-headed shuttling agent.

In yet another aspect, there is provided a process and the resulting polymer, the process comprising polymerizing one or more olefin monomers in the presence of an olefin polymerization catalyst and a dual-headed or multi-headed shuttling agent (MSA) in a polymerization reactor or zone thereby causing the formation of at least some quantity of an initial polymer joined with the remnant of the dual-headed or multi-headed shuttling agent within the reactor or zone; discharging the reaction product from the first reactor or zone to a second polymerization reactor or zone operating under polymerization conditions that are distinguishable from those of the first polymerization reactor or zone; transferring at least some of the initial polymer joined with the remnant of the dual-headed or multi-headed shuttling agent to an active catalyst site in the second polymerization reactor or zone by means of at least one remaining shuttling site of the dual-headed or multi-headed shuttling agent; and conducting polymerization in the second polymerization reactor or zone so as to form a second polymer segment bonded to some or all of the initial polymer by means of a remnant of the dual-headed or multi-headed shuttling agent, the second polymer segment having distinguishable polymer properties from the initial polymer segment.

During the polymerization, the reaction mixture is contacted with the activated catalyst composition according to any suitable polymerization conditions. The process can be generally characterized by use of elevated temperatures and pressures. Hydrogen may be employed as a chain transfer agent for molecular weight control according to known techniques, if desired. As in other similar polymerizations, it is generally desirable that the monomers and solvents employed be of sufficiently high purity that catalyst deactivation or premature chain termination does not occur. Any suitable technique for monomer purification such as devolatilization at reduced pressure, contacting with molecular sieves or high surface area alumina, or a combination of the foregoing processes may be employed.

Supports may be employed in the present methods, especially in slurry or gas-phase polymerizations. Suitable supports include solid, particulated, high surface area, metal oxides, metalloid oxides, or mixtures thereof (interchangeably referred to herein as an inorganic oxide). Examples include, but are not limited to talc, silica, alumina, magnesia, titania, zirconia, $Sn_2O_3$, aluminosilicates, borosilicates, clays, and any combination or mixture thereof. Suitable supports preferably have a surface area as determined by nitrogen porosimetry using the B.E.T. method from 10 to 1000 $m^2/g$, and preferably from 100 to 600 $m^2/g$. The average particle size typically is from 0.1 to 500 μm, preferably from 1 to 200 μm, more preferably 10 to 100 μm.

In one aspect of the present disclosure, the catalyst composition and optional support may be spray dried or otherwise recovered in solid, particulated form to provide a composition that is readily transported and handled. Suitable methods for spray drying a liquid containing slurry are well known in the art and usefully employed herein. Preferred techniques for spray drying catalyst compositions for use herein are described in U.S. Pat. Nos. 5,648,310 and 5,672,669.

The polymerization is desirably carried out as a continuous polymerization, for example, a continuous, solution polymerization, in which catalyst components, monomers, and optionally solvent, adjuvants, scavengers, and polymerization aids are continuously supplied to one or more reactors or zones and polymer product continuously removed therefrom. Within the scope of the terms “continuous” and “continuously” as used in this context include those processes in which there are intermittent additions of reactants and removal of products at small regular or irregular intervals, so that, over time, the overall process is substantially continuous. While the multi-centered shuttling agent and the chain shuttling agent(s) (if used) may be added at any point during the polymerization including in the first reactor or zone, at the exit or slightly before the exit of the first reactor, between the first reactor or zone and any subsequent reactor or zone, or even solely to the second reactor or zone, if present, both are typically added at the initial stages of the polymerization. If there exists any difference in monomers, temperatures, pressures or other polymerization conditions within a reactor or between two or more reactors or zones connected in series, polymer segments of differing composition such as comonomer content, crystallinity, density, tacticity, regio-regularity, or other chemical or physical differences, within the same molecule can be formed in the polymers of this disclosure. In such event, the size of each segment or block is determined by the polymer reaction conditions, and typically is a most probable distribution of polymer sizes.

If multiple reactors are employed, each can be independently operated under high pressure, solution, slurry, or gas phase polymerization conditions. In a multiple zone polymerization, all zones operate under the same type of polymerization, such as solution, slurry, or gas phase, but, optionally, at different process conditions. For a solution polymerization process, it is desirable to employ homogeneous dispersions of the catalyst components in a liquid diluent in which the polymer is soluble under the polymerization conditions employed. One such process utilizing an extremely fine silica or similar dispersing agent to produce such a homogeneous catalyst dispersion wherein normally either the metal complex or the cocatalyst is only poorly soluble is disclosed in U.S. Pat. No. 5,783,512. A high pressure process is usually carried out at temperatures from 100° C. to 400° C. and at pressures above 500 bar (50 MPa). A slurry process typically uses an inert hydrocarbon diluent and temperatures of from 0° C. up to a temperature just below the temperature at which the resulting polymer becomes substantially soluble in the inert polymerization medium. For example, typical temperatures in a slurry polymerization are from 30° C., generally from 60° C. up to 115° C., including up to 100° C., depending on the polymer being prepared. Pressures typically range from atmospheric (100 kPa) to 500 psi (3.4 MPa).

In all of the foregoing processes, continuous or substantially continuous polymerization conditions generally are employed. The use of such polymerization conditions, especially continuous, solution polymerization processes, allows the use of elevated reactor temperatures which results in the economical production of the present block copolymers in high yields and efficiencies.

The catalyst may be prepared as a homogeneous composition by addition of the requisite metal complex or multiple complexes to a solvent in which the polymerization will be conducted or in a diluent compatible with the ultimate reaction mixture. The desired cocatalyst or activator and, optionally, a shuttling agent may be combined with the catalyst composition either prior to, simultaneously with, or after combination of the catalyst with the monomers to be polymerized and any additional reaction diluent. Desirably, the MSA is added at the same time.

At all times, the individual ingredients as well as any active catalyst composition are protected from oxygen, moisture, and other catalyst poisons. Therefore, the catalyst components, multi-centered shuttling agent, and activated catalysts are prepared and stored in an oxygen and moisture free atmosphere, generally under a dry, inert gas such as nitrogen.

Without limiting in any way the scope of the disclosure, one means for carrying out such a polymerization process is as follows. In one or more well stirred tank or loop reactors operating under solution polymerization conditions, the monomers to be polymerized are introduced continuously together with any solvent or diluent at one part of the reactor. The reactor contains a relatively homogeneous liquid phase composed substantially of monomers together with any solvent or diluent and dissolved polymer. Preferred solvents include $C_{4-10}$ hydrocarbons or mixtures thereof, especially alkanes such as hexane or mixtures of alkanes, as well as one or more of the monomers employed in the polymerization. Examples of suitable loop reactors and a variety of suitable operating conditions for use therewith, including the use of multiple loop reactors, operating in series, are found in U.S. Pat. Nos. 5,977,251, 6,319,989 and 6,683,149.

Catalyst along with cocatalyst and multi-centered shuttling agent are continuously or intermittently introduced in the reactor liquid phase or any recycled portion thereof at a minimum of one location. The reactor temperature and pressure may be controlled, for example, by adjusting the solvent/monomer ratio or the catalyst addition rate, as well as by use of cooling or heating coils, jackets or both. The polymerization rate can be controlled by the rate of catalyst addition. The content of a given monomer in the polymer product is influenced by the ratio of monomers in the reactor, which is controlled by manipulating the respective feed rates of these components to the reactor. The polymer product molecular weight is controlled, optionally, by controlling other polymerization variables such as the temperature, monomer concentration, or by the previously mentioned multi-centered shuttling agent, or a chain terminating agent such as hydrogen, as is known in the art.

In one aspect of the disclosure, a second reactor is connected to the discharge of a first reactor, optionally by means of a conduit or other transfer means, such that the reaction mixture prepared in the first reactor is discharged to the second reactor without substantial termination of polymer growth. Between the first and second reactors, a differential in at least one process condition may be established. Generally for use in formation of a copolymer of two or more monomers, the difference is the presence or absence of one or more comonomers or a difference in comonomer concentration. Additional reactors, each arranged in a manner similar to the second reactor in the series may be provided as well. Further polymerization is ended by contacting the reactor effluent with a catalyst kill agent such as water, steam or an alcohol or with a coupling agent if a coupled reaction product is desired.

The resulting polymer product is recovered by flashing off volatile components of the reaction mixture such as residual monomer(s) or diluent at reduced pressure, and, if necessary, conducting further devolatilization in equipment such as a devolatilizing extruder. In a continuous process the mean residence time of the catalyst and polymer in the reactor generally is from 5 minutes to 8 hours, for example, from 10 minutes to 6 hours.

In a further aspect of this disclosure, alternatively, the foregoing polymerization may be carried out in a plug flow reactor optionally with a monomer, catalyst, multi-centered shuttling agent, temperature or other gradient established between differing zones or regions thereof, further optionally accompanied by separate addition of catalysts and/or chain shuttling agent, and operating under adiabatic or non-adiabatic polymerization conditions.

In yet a further aspect, the catalyst composition may also be prepared and employed as a heterogeneous catalyst by adsorbing the requisite components on an inert inorganic or organic particulated solid, as previously disclosed. For example, a heterogeneous catalyst can be prepared by co-precipitating the metal complex and the reaction product of an inert inorganic compound and an active hydrogen containing activator, especially the reaction product of a tri($C_{1-4}$ alkyl) aluminum compound and an ammonium salt of a hydroxyaryltris(pentafluorophenyl)borate, such as an ammonium salt of (4-hydroxy-3,5-ditertiarybutylphenyl)tris(pentafluorophenyl)borate. When prepared in heterogeneous or supported form, the catalyst composition may be employed in a slurry or a gas phase polymerization. As a practical limitation, slurry polymerization takes place in liquid diluents in which the polymer product is substantially insoluble. Generally, the diluent for slurry polymerization is one or more hydrocarbons with less than 5 carbon atoms. If desired, saturated hydrocarbons such as ethane, propane, or butane may be used in whole or part as the diluent. As with a solution polymerization, the α-olefin comonomer or a combination of different α-olefin monomers may be used in whole or part as the diluent. Most preferably at least a major part of the diluent comprises the α-olefin monomer or monomers to be polymerized.

In this aspect, for use in gas phase polymerization processes, the support material and resulting catalyst typically can have a median particle diameter from 20 to 200 μm, generally from 30 μm to 150 μm, and typically from 50 μm to 100 μm. For use in slurry polymerization processes, the support can have a median particle diameter from 1 μm to 200 μm, generally from 5 μm to 100 μm, and typically from 10 μm to 80 μm.

Suitable gas phase polymerization process for use herein are substantially similar to known processes used commercially on a large scale for the manufacture of polypropylene, ethylene/α-olefin copolymers, and other olefin polymers. The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported or suspended above a perforated plate or fluidization grid, by a flow of fluidization gas. Suitable gas phase processes which are adaptable for use in the process of this disclosure are disclosed in, for example, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,556,238; 5,541,270; 5,608,019; and 5,616,661.

The use of functionalized derivatives of polymers are also included within the present disclosure. Examples include metallated polymers wherein the metal is the remnant of the catalyst or chain shuttling agent employed, as well as further derivatives thereof. Because a substantial fraction of the polymeric product exiting the reactor is terminated with the multi-centered shuttling agent, further functionalization is relatively easy. The metallated polymer species can be utilized in well known chemical reactions such as those suitable for other alkyl-aluminum, alkyl-gallium, alkyl-zinc, or alkyl-Group 1 compounds to form amine-, hydroxy-, epoxy-, silane, vinylic, and other functionalized terminated polymer products. Examples of suitable reaction techniques that are adaptable for use herein are described in Negishi, "Organometallics in Organic Synthesis", Vol. 1 and 2, (1980), and other standard texts in organometallic and organic synthesis.

Polymer Products

Utilizing the polymerization processes disclosed here, novel polymer compositions, including block copolymers of one or more olefin monomers having the present molecular weight distribution, are readily prepared. Desirable polymers comprise in polymerized form at least one monomer selected from ethylene, propylene, and 4-methyl-1-pentene. Highly desirably, the polymers are interpolymers comprising in polymerized form ethylene, propylene, or 4-methyl-1-pentene and at least one different $C_{2-20}$ α-olefin comonomer, and optionally one or more additional copolymerizable comonomers. Suitable comonomers are selected from diolefins, cyclic olefins, and cyclic diolefins, halogenated vinyl compounds, vinylidene aromatic compounds, and combinations thereof. Generally preferred polymers are interpolymers of ethylene with 1-butene, 1-hexene or 1-octene. Desirably, the polymer compositions disclosed here have an ethylene content from 1 to 99 percent, a diene content from 0 to 10 percent, and a styrene and/or $C_{3-8}$ α-olefin content from 99 to 1 percent, based on the total weight of the polymer. Typically, the polymers of the disclosure have a weight average molecular weight (Mw) from 10,000 to 2,500,000.

The polymers prepared according to this disclosure can have a melt index, $I_2$, from 0.01 to 2000 g/10 minutes, typically from 0.01 to 1000 g/10 minutes, more typically from 0.01 to 500 g/10 minutes, and especially from 0.01 to 100 g/10 minutes. Desirably, the disclosed polymers can have molecular weights, $M_w$, from 1,000 g/mole to 5,000,000 g/mole, typically from 1000 g/mole to 1,000,000, more typically from 1000 g/mole to 500,000 g/mole, and especially from 1,000 g/mole to 300,000 g/mole. The density of the polymers of this disclosure can be from 0.80 to 0.99 g/$cm^3$ and typically, for ethylene containing polymers, from 0.85 g/$cm^3$ to 0.97 g/$cm^3$.

The polymers according to this disclosure may be differentiated from conventional, random copolymers, physical blends of polymers, and block copolymers prepared via sequential monomer addition, fluxional catalysts, or by anionic or cationic living polymerization techniques, by, among other things, their narrow molecular weight distributions. In this aspect, for example, the polymer composition prepared according to this disclosure can be characterized by a polydispersity index (PDI) of from 1.5 to 3.0. For example, the polydispersity index (PDI) of the polymer composition can be from 1.5 to 2.8, from 1.5 to 2.5, or from 1.5 to 2.3.

If present, the separate regions or blocks within each polymer are relatively uniform, depending on the uniformity of reactor conditions, and chemically distinct from each other. That is, the comonomer distribution, tacticity, or other property of segments within the polymer are relatively uniform within the same block or segment. However, the average block length can be a narrow distribution, but is not necessarily so. The average block length can also be a most probable distribution.

In a further aspect, the resulting polymer may be linear or contain one or more branching centers, depending on whether a two-centered-, three-centered-, or higher centered shuttling agent is employed. Desirably, these interpolymers can be characterized by terminal blocks or segments of polymer having higher tacticity or crystallinity from at least some remaining blocks or segments. Even more desirably, the polymer can be a triblock copolymer containing a central polymer block or segment that is relatively amorphous or even elastomeric.

In yet another aspect, the MSA can be a three centered shuttling agent and the resulting polymers are characterized by the presence of long chain branching. In this aspect, there is provided a method for generating long chain branching in olefin polymers without use of a polymerizable functional group, such as a vinyl group. Instead, the LCB branch point may be the remnant of such a three-centered MSA. Because the extent of LCB in the polymer can be controlled by addition of the three centered MSA to a polymerization reaction at the desired rate the resulting process is advantaged over prior art processes.

In a still further aspect of this disclosure, there is provided a polymer composition comprising: (1) an organic or inorganic polymer, preferably a homopolymer of ethylene or of propylene and/or a copolymer of ethylene or propylene with one or more copolymerizable comonomers, and (2) a polymer or combination of polymers according to the present disclosure or prepared according to the process disclosed here.

The inventive polymer products include combinations of two or more polymers comprising regions or segments (blocks) of differing chemical composition. In addition, at least one of the constituents of the polymer combination can contain a linking group which is the remnant of a dual-headed or multi-headed shuttling agent, causing the polymer to possess certain physical properties.

Various additives may be usefully incorporated into the present compositions in amounts that do not detract from the properties of the resultant composition. These additives include, for example, reinforcing agents, fillers including conductive and non-conductive materials, ignition resistant additives, antioxidants, heat and light stabilizers, colorants, extenders, crosslinkers, blowing agents, plasticizers, flame retardants, anti-drip agents, lubricants, slip additives, anti-blocking aids, anti-degradants, softeners, waxes, pigments, and the like, including combinations thereof.

Applications and End Uses

These polymeric products and blends comprising these polymeric products are usefully employed in the preparation of solid articles such as moldings, films, sheets, and foamed objects by molding, extruding, or other processes, and are useful as components or ingredients in adhesives, laminates, polymeric blends, and other end uses. The resulting products can also be used in the manufacture of components for automobiles, such as profiles, bumpers and trim parts; packaging materials; electric cable insulation; and numerous other applications. The polymer composition of this disclosure can be employed in a variety of conventional thermoplastic fabrication processes to produce useful articles, including objects containing at least one film layer, such as a monolayer film, or at least one layer in a multilayer film, prepared by cast, blown, calendered, or extrusion coating processes; molded articles, such as blow molded, injection molded, or rotomolded articles; extrusions; fibers; and woven or non-woven fabrics. Thermoplastic compositions containing the present polymers, include blends with other natural or synthetic polymers and additives, including the previously mentioned reinforcing agents, fillers, ignition resistant additives, antioxidants, heat and light stabilizers, colorants, extenders, crosslinkers, blowing agents, plasticizers, flame retardants, anti-drip agents, lubricants, slip additives, anti-blocking aids, antidegradants, softeners, waxes, and pigments.

Fibers that may be prepared from the present polymers or blends include staple fibers, tow, multicomponent, sheath/core, twisted, and monofilament. Suitable fiber forming processes include spinbonded, melt blown techniques, as disclosed in U.S. Pat. Nos. 4,430,563, 4,663,220, 4,668,566, and 4,322,027, gel spun fibers as disclosed in U.S. Pat. No. 4,413,110, woven and nonwoven fabrics, as disclosed in U.S. Pat. No. 3,485,706, or structures made from such fibers, including blends with other fibers, such as polyester, nylon or cotton, thermoformed articles, extruded shapes, including profile extrusions and co-extrusions, calendared articles, and drawn, twisted, or crimped yarns or fibers. The new polymers described herein are also useful for wire and cable coating operations, as well as in sheet extrusion for vacuum forming operations, and forming molded articles, including the use of injection molding, blow molding process, or rotomolding processes. Compositions containing the olefin polymers can also be formed into fabricated articles such as those previously mentioned using conventional polyolefin processing techniques which are well known to those skilled in the art of polyolefin processing.

Dispersions (both aqueous and non-aqueous) can also be formed using the present polymers or formulations containing the same. Frothed foams containing the polymers disclosed herein can also be formed, using for example the process disclosed in WO 04/021622. The polymers may also be crosslinked by any known means, such as by the use of peroxide, electron beam, silane, azide, or other cross-linking technique. The polymers can also be chemically modified, such as by grafting (for example by use of maleic anhydride (MAH), silanes, or other grafting agent), halogenation, amination, sulfonation, or other chemical modification.

Suitable polymers for blending with the polymers prepared according to this disclosure include thermoplastic and non-thermoplastic polymers including natural and synthetic polymers. Exemplary polymers for blending include polypropylene, (both impact modifying polypropylene, isotactic polypropylene, atactic polypropylene, and random ethylene/propylene copolymers), various types of polyethylene, including high pressure, free-radical LDPE, Ziegler Natta LLDPE, metallocene PE, including multiple reactor PE ("in reactor" blends of Ziegler-Natta PE and metallocene PE, such as products disclosed in U.S. Pat. Nos. 6,545,088, 6,538,070, 6,566,446, 5,844,045, 5,869,575, and 6,448,341, ethylene-vinyl acetate (EVA), ethylene/vinyl alcohol copolymers, polystyrene, impact modified polystyrene, ABS, styrene/butadiene block copolymers and hydrogenated derivatives thereof (SBS and SEBS), and thermoplastic polyurethanes. Homogeneous polymers such as olefin plastomers and elastomers, ethylene and propylene-based copolymers (for example polymers available under the trade designation VERSIFY™ available from The Dow Chemical Company and VISTAMAXX™ available from ExxonMobil) can also be useful as components in blends containing the present polymer composition.

The blends may be prepared by mixing or kneading the respective components at a temperature around or above the melt point temperature of one or both of the components. For most of the present compositions, this temperature may be above 130° C., 145° C., or even above 150° C. Typical polymer mixing or kneading equipment that is capable of reaching the desired temperatures and melt plastifying the mixture may be employed. These include mills, kneaders, extruders (both single screw and twin-screw), Banbury mixers, and calenders. The sequence of mixing and method may depend on the final composition. A combination of Banbury batch mixers and continuous mixers may also be employed, such as a Banbury mixer followed by a mill mixer followed by an extruder.

The blend compositions may contain processing oils, plasticizers, and processing aids. Some rubber processing oils and paraffinic, napthenic or aromatic process oils are all suitable for use. Generally from 0 to 150 parts, more typically 0 to 100 parts, and most typically from 0 to 50 parts of oil per 100 parts of total polymer composition are employed. Higher amounts of oil may tend to improve the processing of the resulting product at the expense of some physical properties. Additional processing aids include conventional waxes, fatty acid salts, such as calcium stearate or zinc stearate, (poly)alcohols including glycols, (poly)alcohol ethers, including glycol ethers, (poly)esters, including (poly)glycol esters, and metal salt-, especially Group 1 or 2 metal or zinc-, salt derivatives thereof.

Compositions according to this disclosure may also contain anti-ozonants and anti-oxidants that are known to a person of ordinary skill. The anti-ozonants may be physical protectants such as waxy materials that come to the surface and protect the part from oxygen or ozone or they may be chemical protectors that react with oxygen or ozone. Suitable chemical protectors include styrenated phenols, butylated octylated phenol, butylated di(dimethylbenzyl)phenol, p-phenylenediamines, butylated reaction products of p-cresol and dicyclopentadiene (DCPD), polyphenolic anitioxidants, hydroquinone derivatives, quinoline, diphenylene antioxidants, thioester antioxidants, and blends thereof. Some representative trade names of such products are Wingstay™ S antioxidant, Polystay™ 100 antioxidant, Polystay™ 100 AZ antioxidant, Polystay™ 200 antioxidant, Wingstay™ L antioxidant, Wingstay™ LHLS antioxidant, Wingstay™ K antioxidant, Wingstay™ 29 antioxidant, Wingstay™ SN-1 antioxidant, and Irganox™ antioxidants. In some applications, the antioxidants and antiozonants used will typically be non-staining and non-migratory.

For providing additional stability against UV radiation, hindered amine light stabilizers (HALS) and UV absorbers may be also used. Suitable examples include Tinuvin™ 123, Tinuvin™ 144, Tinuvin™ 622, Tinuvin™ 765, Tinuvin™ 770, and Tinuvin™ 780, available from Ciba Specialty Chemicals, and Chemisorb™ T944, available from Cytex Plastics, Houston, Tex., USA. A Lewis acid may be additionally included with a HALS compound in order to achieve superior surface quality, as disclosed in U.S. Pat. No. 6,051,681.

For some compositions, additional mixing processes may be employed to pre-disperse the anti-oxidants, anti-ozonants, pigment, UV absorbers, and/or light stabilizers to form a masterbatch, and subsequently to form polymer blends therefrom.

Certain compositions according to the disclosure, especially those containing the remnant of a conjugated diene comonomer, may be subsequently crosslinked to form cured compositions. Suitable crosslinking agents (also referred to as curing or vulcanizing agents) for use herein include sulfur based, peroxide based, or phenolic based compounds. Examples of the foregoing materials are found in the art, including in U.S. Pat. Nos. 3,758,643, 3,806,558, 5,051,478, 4,104,210, 4,130,535, 4,202,801, 4,271,049, 4,340,684, 4,250,273, 4,927,882, 4,311,628, and 5,248,729.

When sulfur based curing agents are employed, accelerators and cure activators may be used as well. Accelerators are used to control the time and/or temperature required for dynamic vulcanization and to improve the properties of the resulting cross-linked article. In one embodiment, a single accelerator or primary accelerator is used. The primary accelerator(s) may be used in total amounts ranging from 0.5 to 4, typically 0.8 to 1.5, phr, based on total composition weight. In another embodiment, combinations of a primary and a secondary accelerator might be used with the secondary accelerator being used in smaller amounts, such as from 0.05 to 3 phr, in order to activate and to improve the properties of the cured article. Combinations of accelerators generally produce articles having properties that are somewhat better than those produced by use of a single accelerator. In addition, delayed action accelerators may be used which are not affected by normal processing temperatures yet produce a satisfactory cure at ordinary vulcanization temperatures. Vulcanization retarders might also be used. Suitable types of accelerators that may be used as disclosed herein are amines, disulfides, guanidines, thioureas, thiazoles, thiurams, sulfenamides, dithiocarbamates and xanthates. In one aspect, typically, the primary accelerator is a sulfenamide. If a second accelerator is used, the secondary accelerator is typically a guanidine, dithiocarbamate or thiuram compound. Certain processing aids and cure activators such as stearic acid and ZnO may also be used. When peroxide based curing agents are used, co-activators or coagents may be used in combination therewith. Suitable coagents include trimethylolpropane triacrylate (TMPTA), trimethylolpropane trimethacrylate (TMPTMA), triallyl cyanurate (TAC), triallyl isocyanurate (TAIC), among others. Use of peroxide crosslinkers and optional coagents used for partial or complete dynamic vulcanization are known in the art and disclosed for example in the publication, "Peroxide Vulcanization of Elastomers", Vol. 74, No 3, July-August 2001.

The degree of crosslinking in a cured composition according to the disclosure may be measured by dissolving the composition in a solvent for a specified duration, and calculating the percent gel or unextractable rubber. The percent gel normally increases with increasing crosslinking levels. For cured articles according to this disclosure, the percent gel content is desirably in the range from 5 to 100 percent.

The present compositions and blends thereof may also uniquely possess improved melt strength properties due to the presence of the high molecular weight component and unique molecular weight distribution, thereby allowing the present compositions and blends thereof to be usefully employed in foam and in thermoforming applications where high melt strength is desired.

Thermoplastic compositions according to this disclosure may also contain organic or inorganic fillers or other additives such as starch, talc, calcium carbonate, glass fibers, polymeric fibers (including nylon, rayon, cotton, polyester, and polyaramide), metal fibers, wire, mesh, flakes or particles, expandable layered silicates, phosphates or carbonates, such as clays, mica, silica, alumina, aluminosilicates or aluminophosphates, carbon whiskers, carbon fibers, nanoparticles including nanotubes and nonofibers, wollastonite, graphite, zeolites, and ceramics, such as silicon carbide, silicon nitride or titanias. Silane based oils or other coupling agents may also be employed for better filler bonding. Additional suitable additives include tackifiers; oils, including paraffinic or napthelenic oils; and other natural and synthetic polymers, including other polymers according to this disclosure.

The polymer compositions of this disclosure, including the foregoing blends, may be processed by conventional molding techniques such as injection molding, extrusion molding, thermoforming, slush molding, over molding, insert molding, blow molding, and other techniques. Films, including multilayer films, may be produced by cast or tentering processes, including blown film processes.

Further Aspects

Various additional elements, aspects, features and/or embodiments of this disclosure are described. For polymerization reactions that employ a dual- or multi-headed CSA as disclosed herein, reactions can be conducted in a batch reactor with ethylene and propylene, for example, along with an activated catalyst. Ethylene has a substantially higher reactivity than propylene in such polymerizations; therefore, the propylene typically is added to excess and the reaction is run beyond full consumption of the ethylene. In this aspect, the final polymer morphology is characterized as containing an ethylene/propylene rubber segment with isotactic propylene on each end.

Further, reagents such as diethyl zinc or other single site CSA moieties can be used in varying amounts in the methods and processes of this disclosure to create inhomogeneity in the polymer. In this aspect, the relative amount of the inhomogeneity can be controlled by adding more or less diethyl zinc to the reactor. Additional blocks can be added to the end of the polymer by, for example, the addition of another monomer or transferring the reaction mixture to another reactor.

Generally and in further aspects, dual-headed zinc or aluminum CSAs can be prepared from any precursor structure containing two terminal vinyl groups, and can be used for polymerization as long as the linker does not prevent the olefin polymerization process. For example, the linker can be the product derived from 1,3-divinyltetramethyldisiloxane.

Dual-headed zinc CSAs also can be prepared from any precursor structure containing two alkyl-halide groups. While many of the dual-headed CSAs disclosed here are polymeric, a polymeric or oligomeric CSA is not necessary, as shown. For example, the addition of a sulfur, phosphorous, nitrogen, or oxygen-containing "cap" to the CSA also can lead to the desired polymer architecture. For example, a CSA containing Aryl-O—Zn-alkandiyl-Zn—O-Aryl, where Aryl is any substituted or unsubstituted aryl group that is compatible with the olefin polymerization process, also can function in the same manner as a polymeric dual-headed CSA and may be especially useful in process conditions that are not ideal for the polymeric or oligomeric CSAs disclosed here.

Another aspect of the disclosure provides for the catalyst and activator (or activated catalyst) and CSA being fed to a continuous reactor containing ethylene and excess propylene, which are polymerized to form a rubber. The continuous reactor can feed into a tube where either the ethylene is removed or consumed, and crystalline polypropylene is formed. This propylene polymerization proceeds to form a triblock comprised of rubber midblock, capped at each end with a crystalline polypropylene endblock. The process also can be run in multiple batch reactors to form multiblocks. For example, running the process in two reactors would be expected to lead to a symmetric triblock. The process also can be run in a single reactor where reactor environment can be changed during or throughout the polymerization, allowing the formation of different types of olefin polymers. Generally, the processes, methods, and CSAs disclosed herein can be extended to a variety of monomers to yield multiblock copolymers encompassing a broad distribution of polymer composition properties.

Testing Methods

In one aspect of the foregoing disclosure and the examples that follow, the following analytical techniques may be employed to characterize the resulting polymer.

Molecular Weight Determination

Molecular weights are determined by optical analysis techniques including deconvoluted gel permeation chromatography coupled with a low angle laser light scattering detector (GPC-LALLS) as described by Rudin, A., "Modern Methods of Polymer Characterization", John Wiley & Sons, New York (1991) pp. 103-112.

Standard CRYSTAF Method

Branching distributions are determined by crystallization analysis fractionation (CRYSTAF) using a CRYSTAF 200 unit commercially available from PolymerChar, Valencia, Spain. The samples are dissolved in 1,2,4 trichlorobenzene at 160° C. (0.66 mg/mL) for 1 hr and stabilized at 95° C. for 45 minutes. The sampling temperatures range from 95 to 30° C. at a cooling rate of 0.2° C./min. An infrared detector is used to measure the polymer solution concentrations. The cumulative soluble concentration is measured as the polymer crystallizes while the temperature is decreased. The analytical derivative of the cumulative profile reflects the short chain branching distribution of the polymer. The CRYSTAF peak temperature and area are identified by the peak analysis module included in the CRYSTAF Software (Version 2001. b, PolymerChar, Valencia, Spain). The CRYSTAF peak finding routine identifies a peak temperature as a maximum in the dW/dT and the area between the largest positive inflections on either side of the identified peak in the derivative curve.

DSC Standard Method

Differential Scanning calorimetry results are determined using a TAI model Q1OOO DSC equipped with an RCS cooling accessory and an autosampler. A nitrogen purge gas flow of 50 ml/min is used. The sample is pressed into a thin film and melted in the press at 175° C. and then air-cooled to room temperature (25° C.). About 10 mg of material in the form of a 5-6 mm diameter disk is accurately weighed and placed in an aluminum foil pan (ca 50 mg) which is then crimped shut. The thermal behavior of the sample is investigated with the following temperature profile. The sample is rapidly heated to 180° C. and held isothermal for 3 minutes in order to remove any previous thermal history. The sample is then cooled to −40° C. at 10° C./min cooling rate and held at −40° C. for 3 minutes. The sample is then heated to 150° C. at 10° C./min heating rate. The cooling and second heating curves are recorded.

The DSC melting peak is measured as the maximum in heat flow rate (W/g) with respect to the linear baseline drawn between −30° C. and end of melting. The heat of fusion is measured as the area under the melting curve between −30° C. and the end of melting using a linear baseline.

GPC Method

The gel permeation chromatographic system consists of either a Polymer Laboratories Model PL-210 or a Polymer Laboratories Model PL-220 instrument. The column and carousel compartments are operated at 140 C.°. Three Polymer (Laboratories 10-micron Mixed-B columns are used. The solvent is 1,2,4 trichlorobenzene. The samples are prepared at a concentration of 0.1 grams of polymer in 50 milliliters of solvent containing 200 ppm of butylated hydroxytoluene (BHT). Samples are prepared by agitating lightly for 2 hours at 160° C. The injection volume used is 100 microliters and the flow rate is 1.0 ml/minute.

Calibration of the GPC column set is performed with 21 narrow molecular weight distribution polystyrene standards with molecular weights ranging from 580 to 8,400,000, arranged in 6 "cocktail" mixtures with at least a decade of separation between individual molecular weights. The standards are purchased from Polymer Laboratories (Shropshire, UK). The polystyrene standards are prepared at 0.025 grams in 50 milliliters of solvent for molecular weights equal to or greater than 1,000,000 and 0.05 grams in 50 milliliters of solvent for molecular weights less than 1,000,000. The polystyrene standards are dissolved at 80° C. with gentle agitation for 30 minutes. The narrow standards mixtures are run first and in order of decreasing highest molecular weight component to minimize degradation. The polystyrene standard peak molecular weights are converted to polyethylene molecular weights using the following equation (as described in Williams and Ward, J. Polym. Sci., Polym. Let., 6, 621 (1968)): $M_{polyethylene}=0.431(M_{polystyrene})$. Polyethylene equivalent molecular weight calculations are performed using Viscotek TriSEC software Version 3.0.

Density

Density measurement are conducted according to ASTM D 1928. Measurements are made within one hour of sample pressing using ASTM D792, Method B.

Flexural/Secant Modulus

Samples are compression molded using ASTM D 1928. Flexural and 2 percent secant moduli are measured according to ASTM D-790.

Dynamic Mechanical Analysis (DMA)

Dynamic Mechanical Analysis (DMA) is measured on compression molded disks formed in a hot press at 180° C. at 10 MPa pressure for 5 minutes and then water cooled in the press at 90° C./min. Testing is conducted using an ARES controlled strain rheometer (TA instruments) equipped with dual cantilever fixtures for torsion testing.

A 1.5 mm plaque is pressed and cut in a bar of dimensions 32 mm×12 mm. The sample is clamped at both ends between fixtures separated by 10 mm (grip separation ΔL) and subjected to successive temperature steps from −100° C. to +200° C. (5° C. per step). At each temperature the torsion modulus G' is measured at an angular frequency of 10 rad/s, the strain amplitude being maintained between 0.1 percent and 4 percent to ensure that the torque is sufficient and that the measurement remains in the linear regime.

An initial static force of 10 g is maintained (auto-tension mode) to prevent slack in the sample when thermal expansion occurs. As a consequence, the grip separation ΔL increases with the temperature, particularly above the melting or softening point of the polymer sample. The test stops at the maximum temperature or when the gap between the fixtures reaches 65 mm.

Melt Properties

Melt Flow Rate (MFR) and Melt index (MI or $I_2$) are measured in accordance with ASTM D1238, Condition 190° C./2.16 kg.

Analytical Temperature Rising Elution Fractionation (ATREF)

Analytical temperature rising elution fractionation (ATREF) analysis is conducted according to the method described in U.S. Pat. No. 4,798,081, the relevant portion of which is incorporated herein by reference. The composition to be analyzed is dissolved in trichlorobenzene and allowed to crystallize in a column containing an inert support (stainless steel shot) by slowly reducing the temperature to 20° C. at a cooling rate of 0.1° C./min. The column is equipped with an infrared detector. An ATREF chromatogram curve is then generated by eluting the crystallized polymer sample from the column by slowly increasing the temperature of the eluting solvent (trichlorobenzene) from 20° C. to 120° C. at a rate of 1.5° C./min.

All publications and patents mentioned in this disclosure are incorporated herein by reference in their entireties, for the purpose of describing and disclosing, for example, the constructs and methodologies that are described in the publications, which might be used in connection with the presently described methods, compositions, articles, and processes. The publications discussed throughout the text are provided solely for their disclosure prior to the filing date of the present application. Nothing herein is to be construed as an admission that the inventors are not entitled to antedate such disclosure by virtue of prior invention. Should the usage or terminology used in any reference that is incorporated by reference conflict with the usage or terminology used in this disclosure, the usage and terminology of this disclosure controls.

Unless indicated otherwise, when a range of any type is disclosed or claimed, for example a range of molecular weights or values of a parameter such as N, and the like, it is intended to disclose or claim individually each possible number that such a range could reasonably encompass, including any sub-ranges encompassed therein. For example, when the Applicants disclose or claim a value of N can be 20, 25, 30, 35, 40, 45, 50, 55, 60, 65, 70, or greater, Applicants' intent is to disclose or claim individually every possible number that such a range could encompass, consistent with the disclosure herein, including any range, sub-range, or combination of ranges encompassed therein. Accordingly, Applicants reserve the right to proviso out or exclude any individual members of such a group, including any sub-ranges or combinations of sub-ranges within the group, that can be claimed according to a range or in any similar manner, if for any reason Applicants choose to claim less than the full measure of the disclosure, for example, to account for a reference that Applicants are unaware of at the time of the filing of the application.

The Abstract of the disclosure is provided to satisfy the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." The Abstract is not intended to be used to construe the scope of the appended claims or to limit the scope of the subject matter disclosed herein. Moreover, any headings are not intended to be used to construe the scope of the appended claims or to limit the scope of the subject matter disclosed herein. Any use of the past tense to describe an example otherwise indicated as constructive or prophetic is not intended to reflect that the constructive or prophetic example has actually been carried out.

EXAMPLES

The following examples are provided as further illustration of the invention and are not to be construed as limiting. The term "overnight", if used, refers to a time of approximately 16-18 hours, the term "room temperature", refers to a temperature of 20-25° C., and the term "mixed alkanes" refers to a commercially obtained mixture of $C_{6-9}$ aliphatic hydrocarbons available under the trade designation Isopar E®, from ExxonMobil Chemicals Inc. In the event the name of a compound herein does not conform to the structural representation thereof, the structural representation shall control. The synthesis of all metal complexes and the preparation of all screening experiments are carried out in a dry nitrogen atmosphere using dry box (glove box) techniques, including running reactions entirely within a dry box under a nitrogen atmosphere. All solvents used are HPLC grade and are dried before their use.

MMAO refers to modified methylalumoxane, a triisobutylaluminum modified methylalumoxane available commercially from AkzoNobel Corporation.

The following catalysts and cocatalyst can be used in accordance with this disclosure.

Catalyst (A1) is [N-(2,6-di(1-methylethyl)phenyl)amido)(2-isopropylphenyl)(α-naphthalen-2-diyl(6-pyridin-2-diyl)methane)]hafnium dimethyl, prepared according to the teachings of WO 03/40195, 2003US0204017, U.S. Ser. No. 10/429,024, filed May 2, 2003, and WO 04/24740.

(A1)

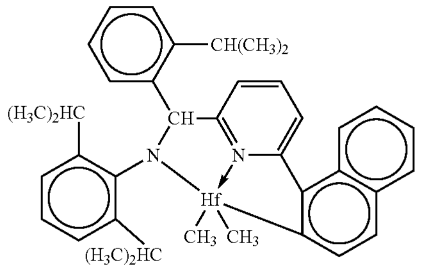

Catalyst (A2) is [N-(2,6-di(1-methylethyl)phenyl)amido)(2-methylphenyl)(1,2-phenylene-(6-pyridin-2-diyl)methane)]hafnium dimethyl, prepared according to the teachings of WO 03/40195, 2003US0204017, U.S. Ser. No. 10/429,024, filed May 2, 2003, and WO 04/24740.

(A2)

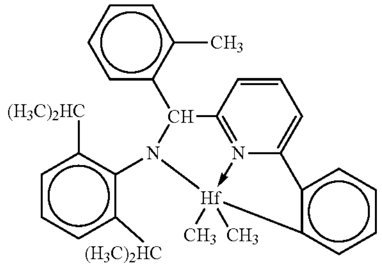

Catalyst (A3) is bis[N,N'''-(2,4,6-tri(methylphenyl)amido)-ethylenediamine]hafnium dibenzyl.

(A3)

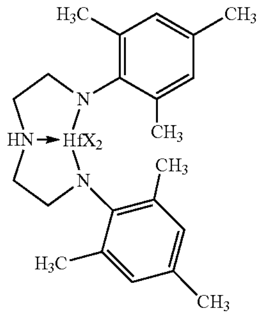

$X = CH_2C_6H_5$

Catalyst (A4) is bis((2-oxoyl-3-(dibenzo-1H-pyrrole-1-yl)-5-(methyl)phenyl)-2-phenoxymethyl)cyclohexane-1,2-diyl zirconium (IV) dibenzyl, prepared substantially according to the teachings of U.S. Pat. No. 6,897,276.

(A4)

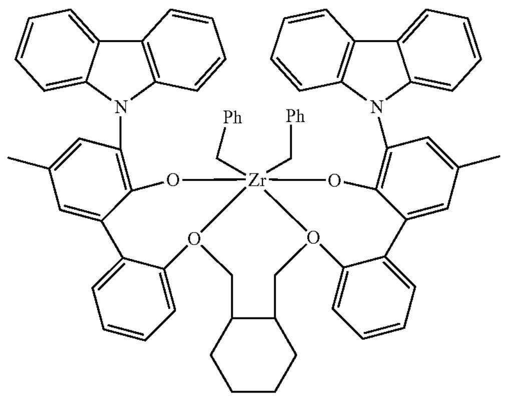

Catalyst (A5) is (bis-(1-methylethyl)(2-oxoyl-3,5-di(t-butyl)phenyl)immino)zirconium dibenzyl.

(A5)

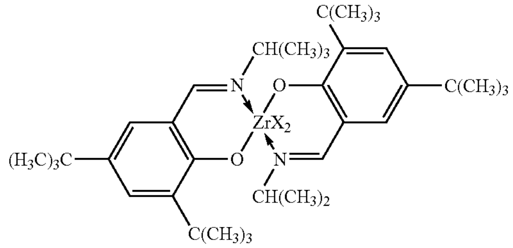

X = $CH_2C_6H_5$

The preparation of catalyst (A5) is conducted according to WO 2007/035493, which is incorporated herein by reference in its entirety.

Catalyst (A6) is bis-(1-(2-methylcyclohexyl)ethyl)(2-oxoyl-3,5-di(t-butyl)phenyl)immino)zirconium dibenzyl.

(A6)

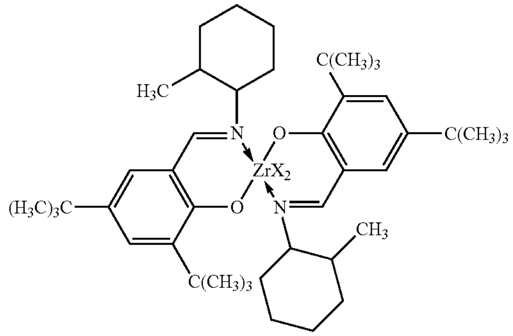

X = $CH_2C_6H_5$

The preparation of catalyst (A6) is conducted according to WO 2007/035493, incorporated herein by reference in its entirety.

Catalyst (A7) is (t-butylamido)dimethyl(3-N-pyrrolyl-1,2,3,3a,7a-η-inden-1-yl)silanetitanium dimethyl prepared substantially according to the techniques of U.S. Pat. No. 6,268,444.

(A7)

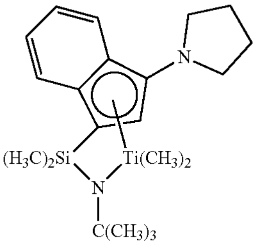

Catalyst (A8) is (t-butylamido)di(4-methylphenyl)(2-methyl-1,2,3,3a,7a-η-inden-1-yl)silanetitanium dimethyl prepared substantially according to the teachings of US-A-2003/004286.

(A8)

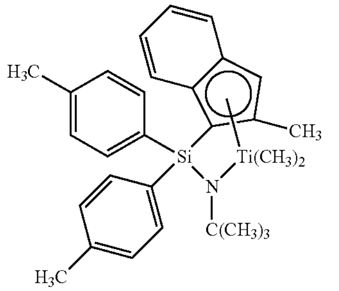

Catalyst (A9) is (t-butylamido)di(4-methylphenyl)(2-methyl-1,2,3,3a,8a-η-s-indacen-1-yl)silanetitanium dimethyl prepared substantially according to the teachings of US-A-2003/004286.

(A9)

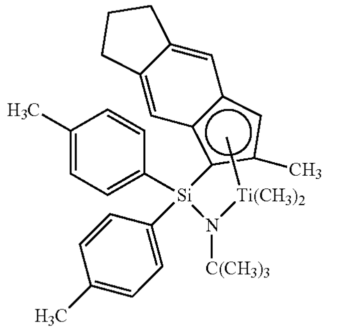

Catalyst (A10) is bis(dimethyldisiloxane)(indene-1-yl)zirconium dichloride available from Sigma-Aldrich.

(A10)

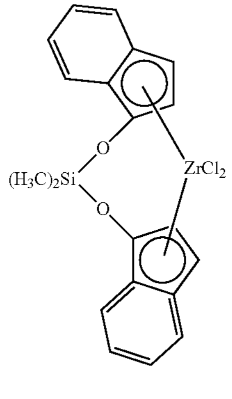

Cocatalyst 1 A mixture of methyldi($C_{14-18}$alkyl)ammonium salts of tetrakis(pentafluorophenyl)borate (also termed armeenium borate), prepared by reaction of a long chain trialkylamine (Armeen™ M2HT, available from Akzo-Nobel, Inc.), HCl and $Li[B(C_6F_5)_4]$, substantially as disclosed in U.S. Pat. No. 5,919,9883, Ex. 2.

Cocatalyst 2 Mixed $C_{14-18}$ alkyldimethylammonium salt of bis(tris(pentafluorophenyl)-alumane)-2-undecylimidazolide, prepared according to U.S. Pat. No. 6,395,671, Ex. 16.

EXAMPLES

Example 1

Preparation and Characterization of a Dual-Headed Zinc Chain Shuttling Agent $Et[Zn(CH_2)_{10}]_N ZnEt$ Referring to Scheme 3, a sample of triethylborane (6.2 g, 63 mmol) is weighed into a 4 oz. glass jar. A PTFE-coated stir bar is added and stirring is initiated. Borane (3.0 mL of neat dimethylsulfide complex, 32 mmol) is added slowly to the stirred liquid. The resulting colorless liquid is stirred for 2 hours at room temperature, after which time the liquid is cooled to −40° C., and 1,9-decadiene (2.9 mL, 16 mmol) is added slowly. The temperature of the solution is allowed to increase slowly to room temperature, and stirring is continued for 1 hour. NMR spectra are taken of the crude material, which demonstrates complete consumption of the olefin. Excess diethylborane is removed in vacuo to leave behind a colorless oil. The mixture is cooled to −40° C. in a freezer. The mixture then is removed and diethyl zinc (5.8 g, 47 mmol) that has been pre-cooled to −40° C. is added dropwise to the mixture. A significant amount of white solid is observed to form in the jar as diethyl zinc is added. The mixture is stirred overnight at room temperature, after which time grey solid is observed in the reaction mixture. Toluene (about 30 mL) is added and the mixture is stirred while heating at 55° C. to dissolve the product. The mixture is decanted and the solution filtered through a 0.45 micron frit. The solution is placed in a freezer at −40° C. The white solid is isolated and dried under vacuum. The solid is re-dissolved in 20 mL toluene at 60° C. and the solvent removed in vacuo at 35° C. to remove excess diethylzinc. After drying under vacuum for 2 hours at 40° C., the mass of the product is 1.3 g.

The molar ratio of Zn:B is preferably greater than 1, to reduce or minimize any excess $Et_2B(CH_2)_nBEt_2$ present in the mixture. The value of N is controlled either by placing the dual headed chain shuttling agent under vacuum to remove $ZnR^1_2$ (to increase N) or by adding more $ZnR^1_2$ to the dual headed chain shuttling agent (to decrease N).

Both $^1H$ and $^{13}C\{^1H\}$ NMR spectra are recorded in $d_8$-THF and are consistent with a polymer or oligomer containing Zn-octyl-Zn units. The NMR data shows that the zinc-ethyl groups are present at a level of 2% of the zinc-decyl-zinc groups. These data indicate that the value of N for the $Et[Zn(CH_2)_{10}]_N ZnEt$ prepared in this manner ranges from about 20 to about 150.

Scheme 3

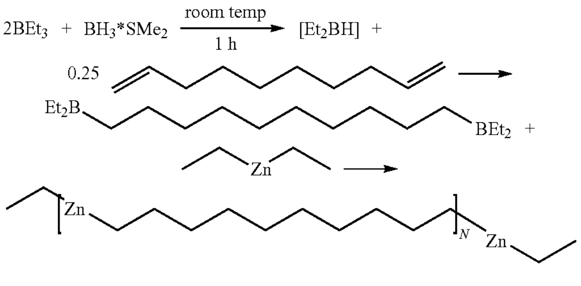

The results and conditions used for the polymerization of ethylene (E) and propylene (P) are provided in Table 3. The dual-headed CSA (abbreviated DH CSA) was loaded as a slurry in toluene into the Parr reactor for the runs. Both $T_m$ and $T_g$ were determined by DSC (Differential Scanning calorimetry). Common conditions for Runs 1-5 are as follows: Temperature, 60° C.; IPE, 600 grams; P, 169 grams; E, 15 grams; catalyst precursor [N-(2,6-di(1-methylethyl)phenyl)amido)(2-isopropylphenyl)(α-naphthalen-2-diyl(6-pyridin-2-diyl)methane)]hafnium dimethyl (catalyst A1). As these data illustrate, very low polydispersities can be realized in the resulting copolymers using the CSAs as disclosed herein.

TABLE 3

Polymer properties and conditions for the polymerization of ethylene (E) and propylene (P). [A]

| Run [B] No. | P (psi) | ΔP (psi) | Run Time (min) | Catalyst µmoles | Catalyst Metal | Act. µmoles | CSA Name(s) | CSA µmoles | ΔT (° C.) |
|---|---|---|---|---|---|---|---|---|---|
| 1 | 187.8 | 37.7 | 11 | 5 | Hf | 6 | DioctZinc | 750 | 4.51 |
| 2 | 222.9 | 16.4 | 5 | 5 | Hf | 6 | DH CSA | 750 | 7.78 |
| 3 | 221.3 | 52.4 | 30 | 2.5 | Hf | 3 | DH CSA | 750 | 9.37 |
| 4 | 221.8 | 66.6 | 30 | 2.5 | Hf | 3 | DH CSA/ 15% DEZ | 625 | 6.57 |
| 5 | 218.3 | 87.5 | 102 | 2 | Hf | 2.4 | DH CSA | 917 | 10.79 |

TABLE 3-continued

Polymer properties and conditions for the polymerization of ethylene (E) and propylene (P). [A]

| Run [B] No. | Yield (g) | Efficiency (g poly/ g Metal) | Tg (° C.) | Tm (° C.) | ΔH (J/g) | Mn (g/mole) | Mw (g/mole) | Mw/Mn |
|---|---|---|---|---|---|---|---|---|
| 1 | 68.5 | 76,755 | −45.8 | 146.5 | 23.6 | 14,385 | 104,869 | 7.29 |
| 2 | 24.4 | 27,340 | −53.1 | none | | 28,939 | 94,630 | 3.27 |
| 3 | 42.7 | 95,692 | −47.3 | none | | 71,482 | 158,689 | 2.22 |
| 4 | 53.6 | 120,119 | −47.8 | 122.4 | 16.0 | 124,614 | 267,921 | 2.15 |
| 5 | 63.1 | 176,761 | −53.3 | 139.7 | 28.9 | 303,501 | 905,043 | 2.98 |

[A] Abbreviations: DioctZinc, $Zn(C_8H_{17})_2$; DH CSA, Dual-Headed Chain Shuttling Agent $Et[Zn(CH_2)_{10}]_N ZnEt$, shown in Scheme 3 of Example 1; Hf catalyst, catalyst precursor [N-(2,6-di(1-methylethyl)phenyl)amido)(2-isopropylphenyl)(α-naphthalen-2-diyl(6-pyridin-2-diyl)methane)]hafnium dimethyl (A1), (CAS# 52196-95-4); Activator, $R_2N(H)Me\ B(C_6F_5)_4$, R = hydrogenated tallowalkyl ($C_{14-18}$ alkyl) (CAS number 200644-82-2).
[B] Common conditions for Runs 1-5: Temperature, 60° C.; IPE, 600 grams; P, 169 grams; E, 15 grams.

Example 2

Controlling Values of N in the Dual-Headed Chain Shuttling Agents

As provided here, the dual-headed chain shuttling agents of the formulas $R^1[M^A\text{-}R^2—]_N\text{-}M^AR^1$ and $R^1[M^BR^1—R^2—]_N M^B(R^1)_2$ are characterized by having values of N>1. As illustrated in Schemes 1 and 2, the rapid room temperature exchange of zinc-hydrocarbyl groups between and among dihydrocarbyl zinc molecules is used to adjust the value or range of values of N in the chain shuttling agents. This rapid and reversible equilibrium aspect allows the value of N to be lowered by combining a known amount of $ZnR^1_2$ such as a dialkyl zinc, with a known amount of the dual-headed CSA. Similarly, the value of N can be increased by dissolving the dual headed zinc chain shuttling agent in a solvent such as toluene and placing the solution under vacuum. In this latter case, the more volatile $ZnR^1_2$, for example $ZnEt_2$, is removed by vacuum, driving the equilibrium away from lower values of N toward higher N values.

The ratio of $R^2$ to $R^1$ moieties can be measured by $^1H$ NMR and $^{13}C\{^1H\}$ NMR spectroscopy and used to determine the average value or range of values of N for the dual-headed CSAs such as $Et[ZnCH_2CH_2]_N ZnEt$ prepared in this manner.

Example 3

Preparation and Utility of Other Dual-Headed Chain Shuttling Agents

Referring to Scheme 3 and Example 1, a large number of dual-headed chain shuttling agents (DH CSAs) having the general formulas $R^1[Zn—R^2—]_N ZnR^1$, $R^1[Mg—R^2—]_N MgR^1$, $R^1[BR^1—R^2—]_N BR^1_2$, $R^1[AlR^1—R^2—]_N AlR^1_2$, and $R^1[GaR^1—R^2—]_N GaR^1_2$, are prepared using methods analogous to that described in Example 1, and are expected to provide similar polymer and polymerization results to those described in Table 3. Examples of DH CSAs are shown in Table 4.

TABLE 4

Examples of possible dual-headed chain shuttling agents

| General Formula | $R^1$ | $R^2$ | Average N |
|---|---|---|---|
| $R^1[Zn—R^2—]_N ZnR^1$ | Et | $(CH_2)_6$ | 3-20 |
| | Me | $(CH_2)_8$ | 5-10 |
| | Et | $(CH_2)_{10}$ | 120-150 |
| | Pr | $(CH_2)_5$ | 12-25 |
| | Et | $O[SiMe_2(CH_2)_2]_2$ | 20-40 |

TABLE 4-continued

Examples of possible dual-headed chain shuttling agents

| General Formula | $R^1$ | $R^2$ | Average N |
|---|---|---|---|
| $R^1[Mg—R^2—]_N MgR^1$ | Et | $(CH_2)_8$ | 20-30 |
| | Me | $(CH_2)_4$ | 75-95 |
| | Et | $(CH_2)_{10}$ | 4-6 |
| $R^1[BR^1—R^2—]_N BR^1_2$ | Et | $(CH_2)_7$ | 6-20 |
| | Et | $(CH_2)_8$ | 50-80 |
| | Me | $(CH_2)_{10}$ | 45-80 |
| $R^1[AlR^1—R^2—]_N AlR^1_2$ | Et | $(CH_2)_7$ | 10-30 |
| | Me | $(CH_2)_8$ | 5-8 |
| | Et | $(CH_2)_{10}$ | 40-60 |
| | Pr | $O[SiMe_2(CH_2)_3]_2$ | 6-12 |
| | Me | $(CH_2)_5$ | 15-40 |
| $R^1[GaR^1—R^2—]_N GaR^1_2$ | Et | $(CH_2)_6$ | 20-40 |
| | Et | $(CH_2)_9$ | 10-12 |
| | Et | $(CH_2)_{10}$ | 55-85 |

Example 4

Predicted Mw and Polydispersity Index for Polymers Obtained Using Linear Dual-Headed Chain Shuttling Agents of Varying Lengths A series of calculations were carried out in order to estimate the molecular weight (Mw) and polydispersity index (PDI=Mw/Mn) of the ethylene-propylene block copolymers prepared using linear, dual-headed zinc chain shuttling agents of varying lengths. These calculations are the result of a statistical analysis of the copolymer, based on the assumption that each R group's eligible valencies grow a most probably distributed kinetic chain, when dual-headed chain shuttling agents having the following formula were employed:

$$R^1—[Zn—R^2—]_N Zn—R^1,$$

wherein $R^1$ in each occurrence is a monovalent hydrocarbyl moiety;

$R^2$ in each occurrence is independently a hydrocarbadiyl having from 2 to 20 carbon atoms, inclusive; and N in each occurrence is an integer from 2 to 50, inclusive.

Thus, examples of chain shuttling agents encompassed by this disclosure include those with N>1. The following structure illustrates the difference between a dual-headed CSA site (D) which constitutes each alkandiyl zinc bond and a mono-headed CSA site (M) which constitutes each alkyl zinc bond. Referring to this structure as a guideline, when N>1, the ratio of multi-headed sites to mono-headed sites, abbreviated Q, will constitute the ratio of dual-headed CSA sites (D) to mono-headed CSA sites (M), for the linear dual-headed chain shuttling agents of zinc, because all the multi-headed sites are all dual-headed. In this case, the value of Q is equal to N, and also equal to the number of zinc atoms in the CSA minus 1. The following Table 5 illustrates this concept for some dual-headed chain shuttling agents of the formula $R^1$—[Zn—$R^2$—$]_N$Zn—$R^1$.

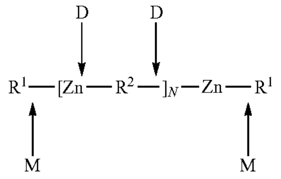

TABLE 5

| Features of Linear Dual-Headed Chain Shuttling Agents of Zinc | | | | |
|---|---|---|---|---|
| N | Zinc Atoms | D Sites | M Sites | Q = D/M |
| 1 | 2 | 2 | 2 | 1 |
| 2 | 3 | 4 | 2 | 2 |
| 3 | 4 | 6 | 2 | 3 |
| 4 | 5 | 8 | 2 | 4 |
| 5 | 6 | 10 | 2 | 5 |
| 6 | 7 | 12 | 2 | 6 |
| 7 | 8 | 14 | 2 | 7 |
| 8 | 9 | 16 | 2 | 8 |

As the length of the dual-headed CSA molecule and the value of N increase, the ratio of dual-headed CSA sites (D) to mono-headed CSA sites (M) also increases, and the resulting polymer composition properties can be altered, Table 6. For example, the polydispersity of the resulting ethylene copolymers prepared using increasingly longer dual-headed CSA is shown to decrease as Q increases, Table 6. The first row of Table 6 provides calculations for the dual headed CSA having the formula $R^1$—Zn—$R^2$—Zn—$R^1$, where N and Q are 1 in the formula $R^1$—[Zn—$R^2$—$]_N$Zn—$R^1$. Thus, as the value of Q increases, the overall molecular weight increases while polydispersity decreases and approach the values for the dual headed CSA, calculated as having a PDI of 1.5.

TABLE 6

| Predicted Overall Mw and Polydispersity for Linear Dual Headed CSA's versus Q.[A] | | | | | | | | |
|---|---|---|---|---|---|---|---|---|
| | Overall | | Single Headed | | | Dual Headed | | |
| N & Q | Mw | PDI | F(mass) | Mw | PDI | F(mass) | Mw | PDI |
| 1 | 1.250M | 1.875 | 0.500 | M | 2 | 0.500 | 1.5M | 1.5 |
| 2 | 1.333M | 1.778 | 0.333 | M | 2 | 0.667 | 1.5M | 1.5 |
| 3 | 1.375M | 1.719 | 0.250 | M | 2 | 0.750 | 1.5M | 1.5 |
| 4 | 1.400M | 1.680 | 0.200 | M | 2 | 0.800 | 1.5M | 1.5 |
| 5 | 1.417M | 1.653 | 0.167 | M | 2 | 0.833 | 1.5M | 1.5 |
| 6 | 1.429M | 1.633 | 0.143 | M | 2 | 0.857 | 1.5M | 1.5 |
| 7 | 1.438M | 1.617 | 0.125 | M | 2 | 0.875 | 1.5M | 1.5 |
| 8 | 1.444M | 1.605 | 0.111 | M | 2 | 0.889 | 1.5M | 1.5 |
| 9 | 1.450M | 1.595 | 0.100 | M | 2 | 0.900 | 1.5M | 1.5 |
| 10 | 1.455M | 1.587 | 0.091 | M | 2 | 0.909 | 1.5M | 1.5 |
| 11 | 1.458M | 1.580 | 0.083 | M | 2 | 0.917 | 1.5M | 1.5 |
| 12 | 1.462M | 1.574 | 0.077 | M | 2 | 0.923 | 1.5M | 1.5 |
| 13 | 1.464M | 1.569 | 0.071 | M | 2 | 0.929 | 1.5M | 1.5 |
| 14 | 1.467M | 1.564 | 0.067 | M | 2 | 0.933 | 1.5M | 1.5 |
| 15 | 1.469M | 1.561 | 0.063 | M | 2 | 0.938 | 1.5M | 1.5 |
| 16 | 1.471M | 1.557 | 0.059 | M | 2 | 0.941 | 1.5M | 1.5 |
| 17 | 1.472M | 1.554 | 0.056 | M | 2 | 0.944 | 1.5M | 1.5 |
| 18 | 1.474M | 1.551 | 0.053 | M | 2 | 0.947 | 1.5M | 1.5 |
| 19 | 1.475M | 1.549 | 0.050 | M | 2 | 0.950 | 1.5M | 1.5 |

[A]Mw is the weight average kinetic chain molecular weight.

Example 5

Preparation and Use of Dual-Headed Aluminum Chain Shuttling Agents of the form Al$[(CH_2)_m]_3$Al Aluminum chain shuttling agents of the form Al$[(CH_2)_m]_3$Al generally can be prepared by the following method, as illustrated for the synthesis of Al$[(CH_2)_{10}]_3$Al, Scheme 4.

A 5.000-g sample of triisobutyl aluminum (23.55 mmol) and 5.046 g (36.50 mmol) of 1,9-decadiene were combined in about 30 mL of mesitylene (b.p. 164-165° C.). This mixture was heated to reflux (164-165° C.) for about 4 hours in a 4 oz. vessel connected to a reflux tube, in a glove box. At the reflux temperature of the solvent, it was expected that the byproduct isobutylene would be driven from the reaction solution. After this time, heating was stopped, the mixture was allowed to cool to room temperature, and was maintained at this temperature for about 2.5 days. The product was a gel. The product description in the following scheme is representative of the empirical formula of the CSA product, which is polymeric. Thus, by describing these chain shuttling agents using general formulas such as Al$[(CH_2)_m]_3$Al and illustrating their structures as shown in the following scheme, it is intended to reflect an average stoichiometry and an empirical formula which are meant to include those species in which a single metal's $(CH_2)_m$ moieties bond to more than one additional metal.

Scheme 4

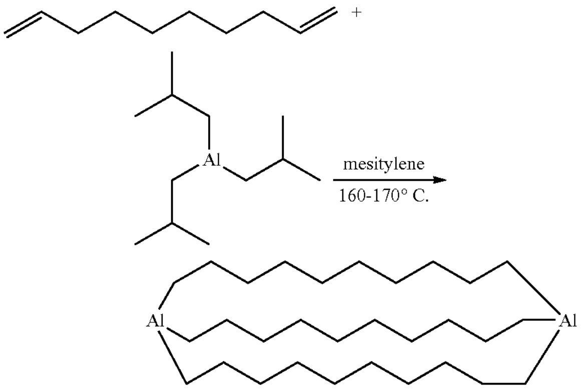

Example 6

Preparation and Use of Cyclic Dual-Headed Magnesium Chain Shuttling Agents of the form Mg$[(CH_2)_m]_2$Mg Cyclic magnesium chain shuttling agents of the formula Mg$[(CH_2)_m]_2$Mg, containing only $R^2$ groups and no $R^1$ groups, generally can be prepared in a manner analogous to the preparation of the corresponding aluminum reagents as illustrated for the synthesis of Al$[(CH_2)_{10}]_3$Al in Scheme 4. Syntheses and examples of similar zinc compounds are found in *J. Organometallic Chem.* 1982, 224, 217, which is incorporated herein by reference in its entirety, and the magnesium compounds also can be prepared in a similar manner. Chain shuttling agents of the formula Mg$[(CH_2)_m]_2$Mg that can be used in the catalytic processes described include those compounds having m=5, 6, 7, 8, and the like.

Example 7

Use of Cyclic Dual-Headed Chain Shuttling Agents to Prepare Acyclic Dual-Headed Chain Shuttling Agents Schemes 5 and 6 illustrate synthetic methods by which cyclic dual-headed chain shuttling agents of the form $M^A[R^2]_2M^A$ could be used to prepare acyclic CSAs of the general formula $R^1[M^A\text{-}R^2—]_N M^A R^1$. The specific examples are applicable to the compounds of the form $M^A[(CH_2)_m]_2M^A$ where $M^A$ is Zn or Mg, and are illustrated for zinc. Scheme 5 demonstrates how the rapid equilibrium among alkyl groups in the zinc system could be used to provide the N>1 CSAs of the form $Et[Zn(CH_2CH_2)]_N ZnEt$ from the N=1 compound $EtZn(CH_2CH_2)ZnEt$ and the cyclic CSA $Zn[(CH_2)_4]_2Zn$. In this scheme, to provide $R^1[M^A\text{-}R^2—]_N M^A R^1$, in which all the $R^2$ moieties are the same.

Scheme 5

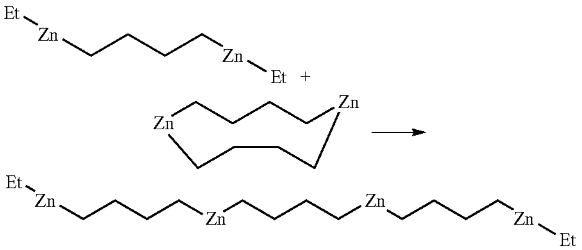

Similarly, Scheme 6 illustrates a similar zinc system could be used to provide the N>1 CSAs from the N=1 compound $EtZn(CH_2)_8ZnEt$ and the cyclic CSA $Zn[(CH_2)_4]_2Zn$, to provide a CSA which contains different $R^2$ moieties. In this scheme, a CSA of the general formula $R^1[M^A\text{-}R^{2B}—]_Z[M^A\text{-}R^{2A}\text{-}M^A][—R^{2B}\text{-}M^A]_Z R^1$ is formed, where $R^{2A}$ is $(CH_2)_8$ and $R^{2B}$ is $(CH_2)_4$. While Z=1 is illustrated in Scheme 6, which corresponds to an N>1 CSA, the addition of further cyclic CSA $Zn[(CH_2)_4]_2Zn$ would be expected to provide Z>1 CSAs, in this specific example, CSAs of the formula $Et[Zn(CH_2)_4]_Z[Zn(CH_2)_8Zn][(CH_2)_4Zn]_Z ZnEt$. As provided in Table 1, structures and compositions such as $R^1[M^A\text{-}R^{2B}—]_Z[M^A\text{-}R^{2A}\text{-}M^A][—R^{2B}\text{-}M^A]_Z R^1$ are readily described by the Newkome nomenclature.

Scheme 6

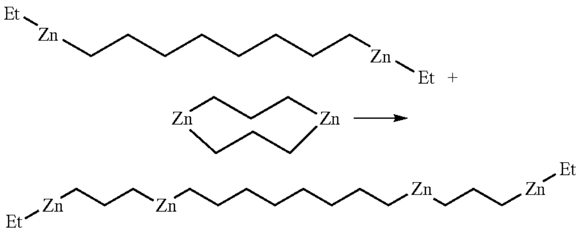

Example 8

Preparation and Utility of a Multi-Headed Zinc Chain Shuttling Agent Precursor, $I[Zn(CH_2)_8]ZnI$ Referring to Scheme 7, a sample of 1,8-diiodooctane (dried over $CaH_2$ and filtered through activated alumina; 10.61 g) was weighed into a 40 mL amber vial containing a PTFE-coated stirbar and diluted with THF to a total volume of about 20 mL. Activated Zn dust (obtained as a THF solution, filtered, and dried in vacuo, 4.55 g) was added slowly to the stirred solution. An exotherm was observed upon addition of the zinc to the 1,8-diiodooctane solution. When the reaction mixture had cooled to ambient temperature, the resulting slurry was heated with stirring at 60° C. for 2.5 days. After this time, the reaction was filtered through Celite and the precipitate was washed with toluene. The filtrate was concentrated in vacuo to yield a thick yellow liquid. Analysis of this material by $^1H$ NMR spectroscopy ($C_6D_6$) confirmed formation of the desired product, $I[Zn(CH_2)_8]ZnI$, along with approximately 20% of $IZnCH_2(CH_2)_6CH_3$, and THF.

Scheme 7

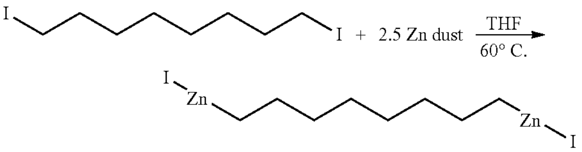

The $I[Zn(CH_2)_8]ZnI$ product of Scheme 7 can be utilized in the same manner as $EtZn(CH_2)_8ZnEt$ in Scheme 6 is used, that is, to vary the value of N and generate new CSAs. If desired, the $I[Zn(CH_2)_8]ZnI$ product can be used in a metathesis reaction such as an alkylation or alkoxylation, to form any number of species of the type $R^1[Zn(CH_2)_8]ZnR^1$, where $R^1$ can be a hydrocarbyl, hydrocarbyl oxide, hydrocarbylamide, tri(hydrocarbyl)silyl, and the like.

Example 9

Preparation and Utility of a Dendritic Zinc Chain Shuttling Agent

This constructive example is described by reference to Scheme 8. In a nitrogen-purged glovebox, diethylborane (1 mmol) is added dropwise to a stirring solution of triallylmethane (10 mmol) in toluene at −40° C. The mixture is stirred for 2 hours at room temperature, after which time the solvent and excess triallylmethane are removed under vacuum. Diethylzinc (1.5 mmol) is added slowly to the hydroborated triallylmethane and the resulting mixture is stirred at room temperature overnight. The resulting mixture is suspended in toluene (15 mL) and filtered through a syringe frit. The resulting solution is placed under vacuum to remove volatile side products and solvent. The resulting zinc compound is hydroborated with diethylborane at −40° C. while dissolved in toluene. The volatiles are removed under vacuum. Excess diethylzinc (about 4 equivalents relative to the zinc compound) is added to the intermediate and the reaction is stirred overnight at room temperature. The resulting mixture is dissolved in toluene, filtered through a syringe frit, and volatile side products are removed under vacuum. The resulting dendritic zinc chain shuttling agent as shown in Scheme 8 is provided. Similar reaction schemes using different reagents to provide the desired dendritic chain shuttling agent are envisioned.

Scheme 8

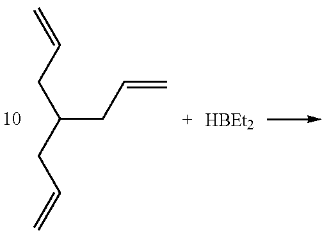

A B

-continued

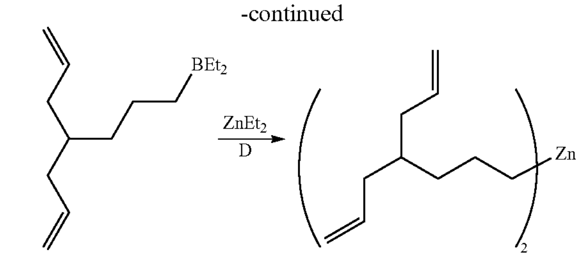

C E

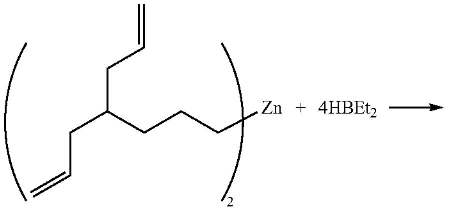

E B

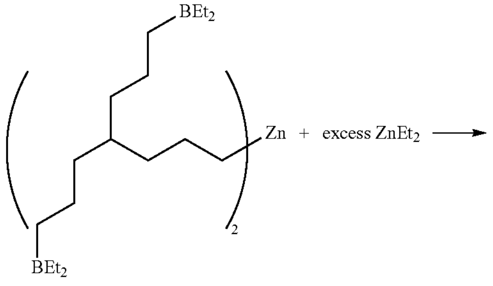

F D

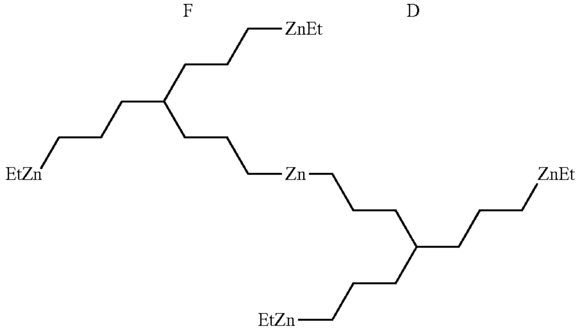

G

Referring to Scheme 8 and the reagents A through G, the following Scheme 9 illustrates one method by which larger dendritic chain shuttling agents could be built up by alternating the reaction sequence of Scheme 8. This scheme is not intended to be limiting, as the use of other reagents such as F can be envisioned to build up the size and complexity of the CSA dendrimer by a somewhat different process.

Scheme 9

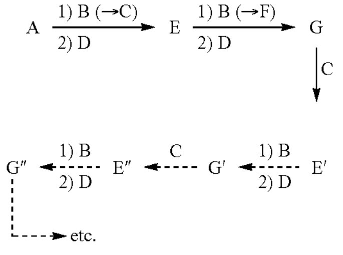

We claim:

1. A chain shuttling agent having the formula:

$R^1[M^A\text{-}R^2—]_N M^A R^1$, $R^1[M^B R^1—R^2—]_N M^B(R^1)_2$, $M^C[R^2]_2M^C$, or $M^B[R^2]_3M^B$;

or an aggregate thereof, a Lewis base-containing derivative thereof, or any combination thereof; wherein $M^A$ is Zn or Mg;

$M^B$ is B, or Ga;

$M^C$ is Mg;

$R^1$ in each occurrence is independently selected from hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 20 carbon atoms, inclusive;

$R^2$ in each occurrence is independently selected from $(CH_2)_m$, $O[(CH_2)_nCH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]_2$, $(R^B)_3SiOSiR^B[(CH_2)_nCH_2CH_2]_2$, or $[Si(R^B)_2(CH_2)_nCH_2CH_2]_2O$; wherein n in each occurrence is independently an integer from 1 to 20, inclusive; m is an integer from 2 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

2. A process for the polymerization of at least one addition polymerizable monomer to form a polymer composition, the process comprising:

contacting at least one addition polymerizable monomer with a catalyst composition under polymerization conditions; wherein the catalyst composition comprises the contact product of at least one polymerization catalyst precursor, at least one cocatalyst, and the chain shuttling agent of claim 1.

3. A multiblock copolymer obtained by a process comprising:

contacting at least one addition polymerizable monomer with a catalyst composition under polymerization conditions; wherein the catalyst composition comprises the contact product of at least one polymerization catalyst precursor, at least one cocatalyst, and a chain shuttling agent having the formula:

$R^1[M^A\text{-}R^2—]_N M^A R^1$, $R^1[M^B R^1—R^2—]_N M^B(R^1)_2$, $M^C[R^2]_2M^C$, or $M^B[R^2]_3M^B$;

or an aggregate thereof, a Lewis base-containing derivative thereof, or any combination thereof; wherein $M^A$ is Zn or Mg;

$M^B$ is B, Al, or Ga;

$M^C$ is Mg;

$R^1$ in each occurrence is independently selected from hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 20 carbon atoms, inclusive;

$R^2$ in each occurrence is independently selected from $(CH_2)_m$, $O[(CH_2)_nCH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]_2$, $(R^B)_3SiOSiR^B[(CH_2)_nCH_2CH_2]_2$, or $[Si(R^B)_2(CH_2)_nCH_2CH_2]_2O$; wherein n in each occurrence is independently an integer from 1 to 20, inclusive; m is an integer from 2 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

4. A catalyst composition comprising the contact product at least one polymerization catalyst precursor, at least one cocatalyst, and a chain shuttling agent having the formula:

$R^1[M^A\text{-}R^2—]_NM^AR^1$, $R^1[M^BR^{1—R2}—]_NM^B(R^1)_2$, $M^C[R^2]_2M^C$, or $M^B\,[R^2]_3M^B$;

or an aggregate thereof, a Lewis base-containing derivative thereof, or any combination thereof; wherein $M^A$ is Zn or Mg;

$M^B$ is B, Al, or Ga;

$M^C$ is Mg;

$R^1$ in each occurrence is independently selected from hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 20 carbon atoms, inclusive;

$R^2$ in each occurrence is independently selected from $(CH_2)_m$, $O[(CH_2)_nCH_2CH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]_2$, $(R^B)_3SiOSiR^B[(CH_2)_nCH_2CH_2]_2$, or $[Si(R^B)_2(CH_2)_nCH_2CH_2]_2O$; wherein n in each occurrence is independently an integer from 1 to 20, inclusive; m is an integer from 2 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

5. A chain shuttling agent represented by the following Newkome dendrimer nomenclature:

$$[C][(R)\overset{G}{N_b}(Z)]N_c,$$

an aggregate thereof, a Lewis base-containing derivative thereof, or any combination thereof; wherein:

C is a core selected from a metal, alkadiyl di(metal), alkatriyl tri(metal), or alkatetrayl tetra(metal), wherein the metal is Zn, Mg, B, Al, or Ga, and any carbon-containing core has from 2 to 20 carbon atoms;

R in each occurrence is a repeat unit selected from an alkadiyl metal, alkatriyl di(metal), or alkatetrayl tri (metal) having from 2 to 20 carbon atoms and a branch multiplicity of $N_b$;

G is the generation of the dendrimer cascade;

Z is a terminal monovalent having up to 20 carbon atoms;

$N_c$, is the branch multiplicity of the core; and the shuttling agent comprises at least one generation of repeat unit R, such that G on average is a number from 2 to 150, inclusive.

6. A process for the polymerization of at least one addition polymerizable monomer to form a polymer composition, the process comprising:

contacting at least one addition polymerizable monomer with a catalyst composition under polymerization conditions;

wherein the catalyst composition comprises the contact product of at least one polymerization catalyst precursor, at least one cocatalyst, and the shuttling agent of claim 5.

7. A multiblock copolymer obtained by the process of claim 6.

8. A catalyst composition comprising the contact product at least one polymerization catalyst precursor, at least one cocatalyst, and the shuttling agent of claim 5.

9. A process for preparing the chain shuttling agent of claim 5 comprising:

a) providing a polyene having the formula $R^AC[(CH_2)_nCH{=}CH_2]_3$ or $C[(CH_2)_nCH{=}CH_2]_4$, wherein n in each occurrence is independently an integer from 0 to 20 and $R^A$ is H or a hydrocarbyl having from 1 to 12 carbon atoms, inclusive; and b) contacting the polyene with a borohydride having the formula $(R^C)_2BH$, wherein $R^C$ is a hydrocarbyl having from 1 to 20 carbon atoms, to form a first composition comprising a partially hydroborated polyene;

c) contacting the first composition with $M^A(R^{1A})_2{}^{or\ MB}(R^{1A})_3$ to form a second composition, comprising $M^A\{CH_2CH_2(CH_2)_nE[(CH_2)_nCH{=}CH_2]_{m-1}\}_2$ or $M^B\{CH_2CH_2(CH_2)_nE[(CH_2)_nCH{=}CH_2]_{m-1}\}_3$wherein $R^{1A}$ in each occurrence is independently a hydrocarbyl having from 1 to 20 carbon atoms, inclusive, optionally substituted with at least one halide, amide, hydrocarbylamide, dihydrocarbylamide, or hydrocarbyloxide;

d) contacting the second composition with $(R^C)_2BH$, followed by contacting the resulting composition with ${}_M{}^A(R^{1A})_2$ or $M^B(R^{1A})_3$ to form a third composition;

e) contacting the third composition with a partially hydroborated polyene prepared according to step b); and f) repeating steps d) and e) any number of times to form a dendrimeric chain shuttling agent.

10. A process for preparing a chain shuttling agent having the formula:

$R^1[M^A\text{-}R^2—]_NM^AR^1$, wherein $M^A$ is Zn or Mg, or $R^{1[MB}R^1—R^{2—]}{}_NM^B(R^1)_2$, wherein $M^B$ is B, Al, or Ga;

or an aggregate thereof, a Lewis base-containing derivative thereof, or any combination thereof; the process comprising:

a) providing an α,ω-diene having the formula $CH_2{=}CH(CH_2)_nCH{=}CH_2$, $O[(CH_2)_nCH{=}CH_2]_2$, $S[(CH_2)_nCH{=}CH_2]_2$, $R^AN[(CH_2)_nCH{=}CH_2]_2$, $(R^B)_2Si[(CH_2)_nCH{=}CH_2]_2$, $(R^B)3SiOSiR^B[(CH_2)_nCH{=}CH_2]_2$, or $[Si(R^B)_2(CH_2)_nCH{=}CH_2]_2O$; wherein n in each occurrence is independently an integer from 0 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive;

b) contacting the α,ω-diene with a borohydride compound having the formula $(R^C)_2BH$, wherein $R^C$ is a hydrocarbyl having from 1 to 20 carbon atoms, to form a first composition; and c) contacting the first composition with $M^A(R^{1A})(R^1)$ or $M^B(R^{1A})(R^1)_2$ to form a second composition comprising the chain shuttling agent;

wherein $R^{1A}$ in each occurrence is independently selected from hydrogen or a hydrocarbyl having from 1 to 20 carbon atoms, inclusive, optionally substituted with at least one halide, amide, hydrocarbylamide, dihydrocarbylamide, or hydrocarbyloxide;

$R^1$ in each occurrence is independently selected from hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 20 carbon atoms, inclusive;

$R^2$ in each occurrence is independently selected from $(CH_2)_m$, $O[(CH_2)_nCH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]_2$, $(R^B)_3SiOSiR^B[(CH_2)_nCH_2CH_2]_2$, or $[Si(R^B)_2(CH_2)_nCH_2CH_2]_2O$; wherein n in each occurrence is independently an integer from 1 to 20, inclusive; m is an integer from 2 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

11. A chain shuttling agent having the formula:

$$R^1[M^BR^1—R^2—]_NM^B(R^1)_2, \text{ or}$$

$$M^B[R^2]_3M^B;$$

or an aggregate thereof, a Lewis base-containing derivative thereof, or any combination thereof; wherein $M^B$ is Al;

$R^1$ in each occurrence is independently selected from hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 20 carbon atoms, inclusive;

$R^2$ in each occurrence is independently selected from $(CH_2)_m$, $O[(CH_2)_nCH_2CH_2]_2$, $S[(CH_2)_nCH_2CH_2]_2$, $R^AN[(CH_2)_nCH_2CH_2]_2$, $(R^B)_2Si[(CH_2)_nCH_2CH_2]_2$, $(R^B)_3SiOSiR^B[(CH_2)_nCH_2CH_2]_2$, or $[Si(R^B)_2(CH_2)_2CH_2CH_2]_2O$; wherein n in each occurrence is independently an integer from 1 to 20, inclusive; m is an integer from 3 to 20, inclusive; $R^A$ is H or a hydrocarbyl having from 1 to 12 carbon atoms, inclusive; and $R^B$ in each occurrence is independently a hydrocarbyl having from 1 to 12 carbon atoms, inclusive; and N, on average, in each occurrence is a number from 2 to 150, inclusive.

* * * * *